(12) United States Patent
Kishi et al.

(10) Patent No.: US 11,730,956 B2
(45) Date of Patent: Aug. 22, 2023

(54) POWER SUPPLY APPARATUS AND MAGNETIC FIELD GENERATION SYSTEM

(71) Applicants: Kazuhito Kishi, Tokyo (JP); Masami Takai, Tokyo (JP); Motokazu Hasegawa, Tokyo (JP); Masataka Akaishi, Tokyo (JP); PUBLIC UNIVERSITY CORPORATION YOKOHAMA CITY UNIVERSITY, Kanagawa (JP)

(72) Inventors: Kazuhito Kishi, Kanagawa (JP); Masami Takai, Tokyo (JP); Motokazu Hasegawa, Kanagawa (JP); Masataka Akaishi, Kanagawa (JP); Masanari Umemura, Kanagawa (JP); Yoshihiro Ishikawa, Kanagawa (JP); Taisuke Akimoto, Kanagawa (JP)

(73) Assignees: Ricoh Company, Ltd., Tokyo (JP); PUBLIC UNIVERSITY CORPORATION YOKOHAMA CITY UNIVERSITY, Kanagawa (JP)

( * ) Notice: Subject to any disclaimer, the term of this patent is extended or adjusted under 35 U.S.C. 154(b) by 1100 days.

(21) Appl. No.: 16/416,764

(22) Filed: May 20, 2019

(65) Prior Publication Data

US 2019/0358448 A1 Nov. 28, 2019

(30) Foreign Application Priority Data

May 23, 2018 (JP) .................................. 2018-099149

(51) Int. Cl.
*A61N 1/32* (2006.01)
*A61N 1/40* (2006.01)
(Continued)

(52) U.S. Cl.
CPC ............... *A61N 1/326* (2013.01); *A61N 1/40* (2013.01); *G03G 15/2039* (2013.01); *H05B 6/04* (2013.01); *H05B 6/06* (2013.01)

(58) Field of Classification Search
CPC . A61N 1/326; A61N 1/40; A61N 2/02; G03G 15/2039; H05B 6/04; H05B 6/06; H05B 6/62
See application file for complete search history.

(56) References Cited

U.S. PATENT DOCUMENTS 8,809,752 B2   8/2014 Yamashita
2016/0213943 A1*  7/2016 Mauger .................. A61N 2/006
(Continued)

FOREIGN PATENT DOCUMENTS

EP    0361797      4/1990
JP    H01-244767   9/1989
(Continued)

OTHER PUBLICATIONS

Office Action dated Nov. 30, 2021 issued with respect to the corresponding Japanese Patent Application No. 2018-099149.

*Primary Examiner* — Amanda K Hulbert
*Assistant Examiner* — Philip C Edwards
(74) *Attorney, Agent, or Firm* — IPUSA, PLLC

(57) ABSTRACT

A power supply apparatus includes a power supply configured to apply an alternating current to a magnetic field generation apparatus; and a controller configured to control the alternating current applied by the power supply. The controller controls the power supply to apply the alternating current having a waveform pattern including a plurality of current waveforms having different frequency spectrums from each other.

11 Claims, 18 Drawing Sheets

(51) Int. Cl.
*H05B 6/06* (2006.01)
*H05B 6/04* (2006.01)
*G03G 15/20* (2006.01)

(56) References Cited

U.S. PATENT DOCUMENTS

2017/0014637 A1* 1/2017 Basser ................ A61N 1/40
2019/0104569 A1* 4/2019 Moon ................. H05B 6/062
2019/0110829 A1* 4/2019 Chieh ................ H05B 6/105

FOREIGN PATENT DOCUMENTS

| | | |
|---|---|---|
| JP | H02-088059 | 3/1990 |
| JP | H03-158176 | 7/1991 |
| JP | 2008-103307 | 5/2008 |
| JP | 4750784 | 8/2011 |
| WO | 2005/115535 | 12/2005 |
| WO | 2018/097185 | 5/2018 |

* cited by examiner

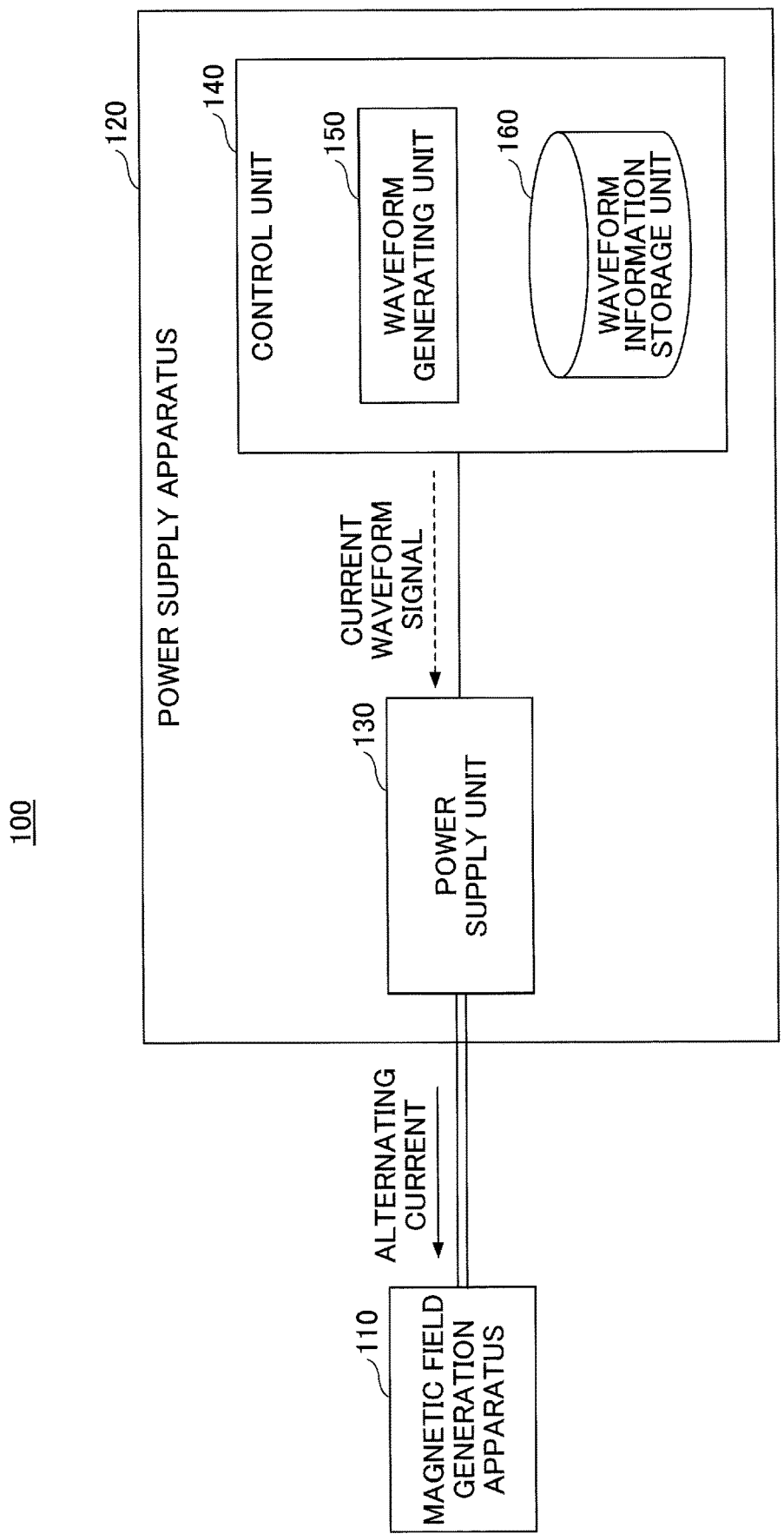

FIG.5
| WAVEFORM INFORMATION | | |
|---|---|---|
| WAVEFORM TYPE | FREQUENCY SPECTRUM | WAVEFORM DATA |
| I | 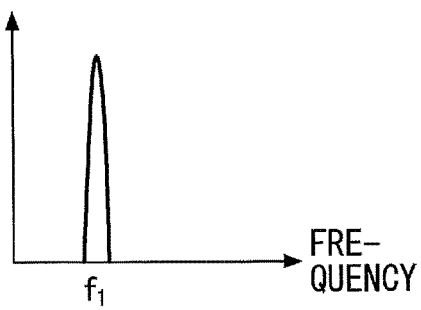 $f_1$ | 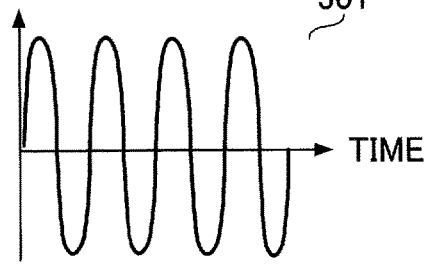 501 |
| ⋮ | ⋮ | ⋮ |
| II | 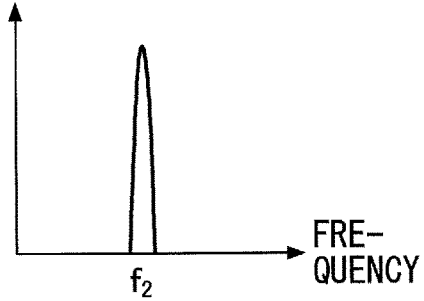 $f_2$ | 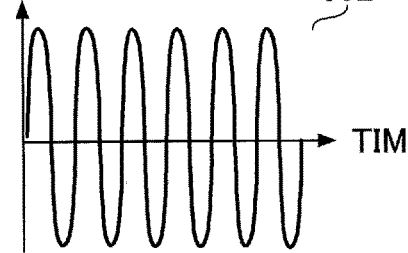 502 |
| ⋮ | ⋮ | ⋮ |
| III | 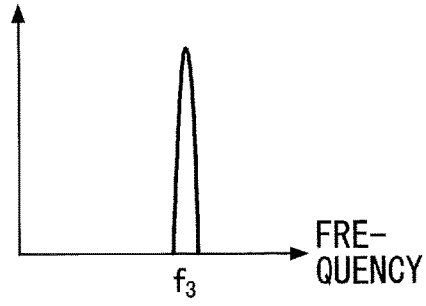 $f_3$ | 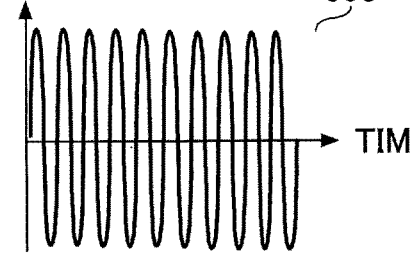 503 |

POWER SUPPLY APPARATUS AND MAGNETIC FIELD GENERATION SYSTEM

CROSS-REFERENCE TO RELATED APPLICATION

The present application is based on and claims priority under 35 U.S.C. § 119 to Japanese Patent Application No. 2018-099149, filed on May 23, 2018, the contents of which are incorporated herein by reference in their entirety.

BACKGROUND OF THE INVENTION

1. Field of the Invention

The present invention relates to a power supply apparatus and a magnetic field generation system.

2. Description of the Related Art

Conventionally, cancer treatment apparatuses using various kinds of therapy have been proposed. For example, Patent Documents 1 and 2 below propose cancer treatment apparatuses that use heating therapy in which tumor cells are heated by dielectric heating or by generating heat in a target material by dielectric heating. In these cancer treatment apparatuses, a method of generating a magnetic field by a coil disposed near the patient's body surface to magnetically heat the patient's body, is used.

Also, Patent Document 3 below proposes a cancer treatment apparatus that uses electric field therapy in which an electric field is applied to cancer cells. The cancer treatment apparatus applies an electric field by placing an electrode on the patient's body surface.

Patent Document 1: Japanese Unexamined Patent Application Publication No. H2-88059
Patent Document 2: Japanese Unexamined Patent Application Publication No. H3-158176
Patent Document 3: Japanese Patent No. 4750784

SUMMARY OF THE INVENTION

An aspect of the present invention provides a power supply apparatus and a magnetic field generation system in which one or more of the disadvantages of the related art are reduced.

According to one aspect of the present invention, there is provided a power supply apparatus including a power supply configured to apply an alternating current to a magnetic field generation apparatus; and a controller configured to control the alternating current applied by the power supply, wherein the controller controls the power supply to apply the alternating current having a waveform pattern including a plurality of current waveforms having different frequency spectrums.

BRIEF DESCRIPTION OF THE DRAWINGS

FIG. 1 is a diagram illustrating an example of a system configuration of a magnetic field generation system according to a first embodiment of the present invention;

FIG. 5 is a diagram illustrating examples of waveform information according to the first embodiment of the present invention;

DETAILED DESCRIPTION OF THE PREFERRED EMBODIMENTS

Figure 2A:
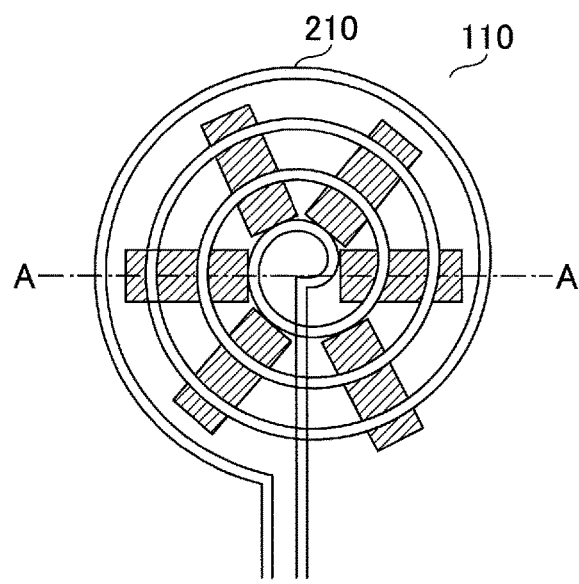
FIGS. 2A to 2C are diagrams illustrating an example of a configuration of a magnetic field generation apparatus according to the first embodiment of the present invention.

The applicant of the present application has discovered that, by applying an alternating magnetic field of a particular frequency to cancer cells, it is possible to achieve a certain effect on inhibiting the growth of cancer cells, and the applicant is considering a cancer treatment apparatus using therapy different from heating therapy or electric field therapy as described in the background above.

However, there are various types of cancer, and even with respect to the same type of cancer, different cancer cells may exhibit different properties. Furthermore, it may be difficult to apply a strong magnetic field from outside the body to cancer cells deep inside the body. Accordingly, in order to improve the effectiveness of inhibiting the growth of cancer cells, there is a need to apply an alternating magnetic field having appropriate frequency components and at an appropriate intensity.

A problem to be addressed by an embodiment of the present invention is to provide a power supply apparatus and a magnetic field generation system capable of applying an appropriate alternating magnetic field.

Embodiments of the present invention will be described by referring to the accompanying drawings. In the specification and drawings of the embodiments, the elements having substantially the same functions are denoted by the same reference numerals, and overlapping descriptions are omitted.

First Embodiment

<System Configuration of Magnetic Filed Generation System—First Embodiment>

First, the system configuration of the magnetic field generation system according to a first embodiment will be described. FIG. 1 is a diagram illustrating an example of a system configuration of a magnetic field generation system according to the first embodiment. As illustrated in FIG. 1, a magnetic field generation system 100 includes a magnetic field generation apparatus 110 and a power supply apparatus 120 for use in medical treatment of tumors.

The magnetic field generation apparatus 110 includes a coil formed in a swirl-like shape and cores, and generates an alternating magnetic field when an alternating current is applied by the power supply apparatus 120.

The power supply apparatus 120 includes a power supply unit 130 and a control unit 140. The power supply unit 130 receives a current waveform signal transmitted from the control unit 140 and outputs an alternating current that corresponds to the received current waveform signal. The power supply unit 130 converts power of a commercial power supply to a high frequency alternating current of 100 [kHz] to 400 [kHz] and outputs the alternating current, based on the received current waveform signal.

A waveform generation program is installed in the control unit 140, and by executing the program, the control unit 140 functions as a waveform generating unit 150. The waveform generating unit 150 reads waveform information from a waveform information storage unit 160 and generates a current waveform signal based on the read waveform information. The waveform generating unit 150 transmits the generated current waveform signal to the power supply unit 130. Accordingly, the control unit 140 can control the alternating current to be applied by the power supply unit 130 to the magnetic field generation apparatus 110.

<Configuration of Magnetic Field Generation Apparatus—First Embodiment>

Figure 2B:
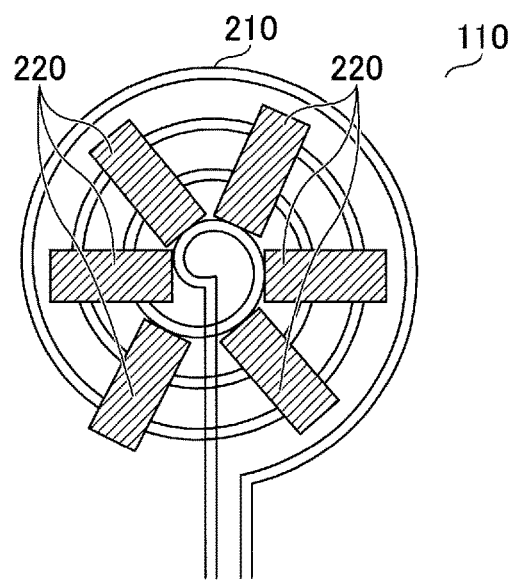
Figure 2C:
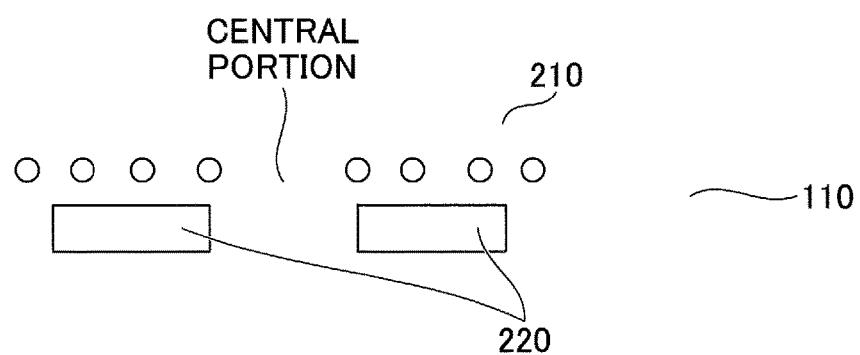

Next, a specific configuration of the magnetic field generation apparatus 110 will be described. FIGS. 2A to 2C are diagrams illustrating an example of a configuration of the magnetic field generation apparatus 110. Among these, FIG. 2A illustrates a view of the magnetic field generation apparatus 110 from the front side, and FIG. 2B illustrates a view of the magnetic field generation apparatus 110 from the rear side. Furthermore, FIG. 2C illustrates a view of the magnetic field generation apparatus 110 from a direction substantially perpendicular to a cross-section cut along a line A-A of the magnetic field generation apparatus 110 in FIG. 2A.

As illustrated in FIG. 2A, the magnetic field generation apparatus 110 includes a coil 210 formed by winding a Litz wire having low loss at high frequencies into a swirl-like shape. Note that in the example of FIG. 2A, the coil 210 is illustrated as being wound with a constant gap in order to clearly indicate that the coil 210 is swirl-like; however, actually, the coil 210 is assumed to be wound without any gaps.

Furthermore, as illustrated in FIG. 2B, the magnetic field generation apparatus 110 includes six cores 220 disposed on the rear side of the coil 210. The six cores 220 are disposed radially outward from the central portion of the swirl-like coil 210. Note that in the cross-section in which the cores 220 are disposed (e.g., the A-A cross-section of FIG. 2A), the coil 210 and the cores 220 are disposed symmetrically with respect to the central portion of the coil 210, respectively, as illustrated in FIG. 2C. Such a cross-sectional disposition allows the magnetic field generated by the coil 210 to be concentrated in the central portion, thereby reducing the leakage magnetic field in the magnetic field generation apparatus 110.

Although not illustrated in FIGS. 2A to 2C, the magnetic field generation apparatus 110 includes a housing for housing the coil 210 and the cores 220, and the coil 210 and the cores 220 are housed in the housing. As described above, the magnetic field generation apparatus 110 is configured such that the coil 210 and the cores 220 do not come into direct contact with the patient.

<Positional Relationship between Direction of Magnetic Field Line and Treatment Target (Diseased Portion)—First Embodiment>

Figure 3A:
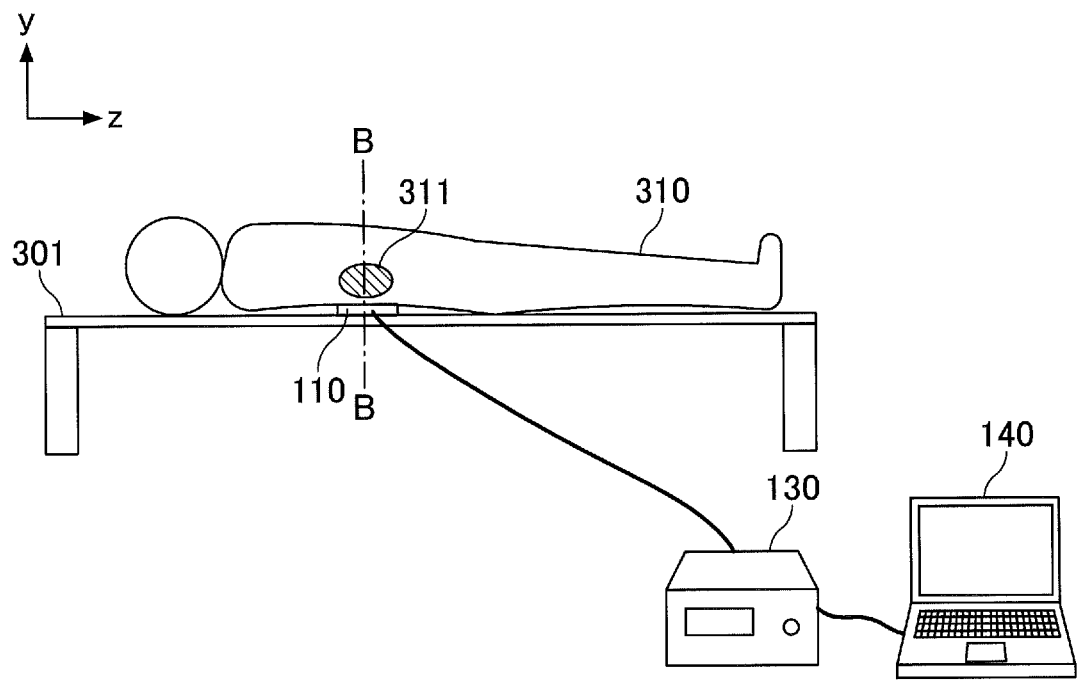
FIGS. 3A and 3B are diagrams illustrating the positional relationship between directions of magnetic field lines of the magnetic field generation apparatus and a diseased portion (treatment target) according to the first embodiment of the present invention.
Figure 3B:
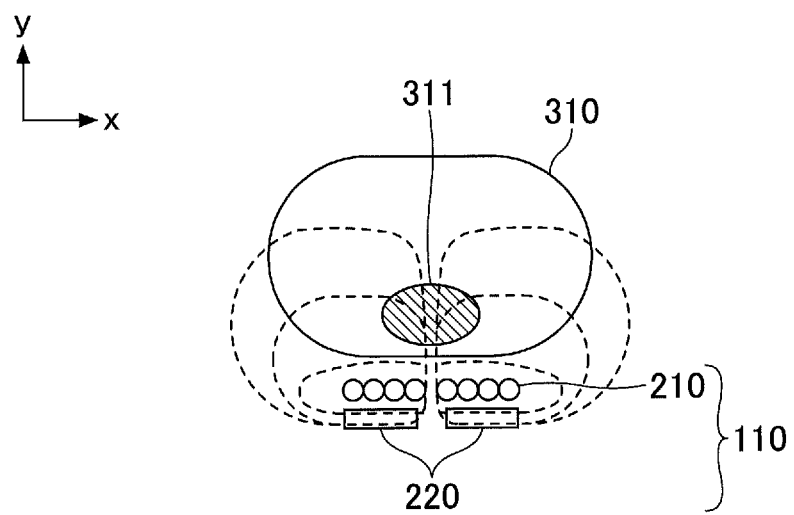

Next, the positional relationship between the direction of the magnetic field line and the diseased portion (hereinafter, "treatment target") of the patient will be described, when an alternating magnetic field is generated in the magnetic field generation apparatus 110. FIGS. 3A and 3B are diagrams illustrating a positional relationship between a direction of a magnetic field line of the magnetic field generation apparatus 110 and the treatment target.

As illustrated in FIG. 3A, the magnetic field generation apparatus 110 is disposed near a treatment target (diseased portion) 311 (in the example of FIG. 3A, a position in the back of a patient 310) of the patient 310 lying supine on a bed 301. In the state illustrated in FIG. 3A, an alternating magnetic field can be applied to the treatment target 311 by applying an alternating current to the magnetic field generation apparatus 110 and generating an alternating magnetic field.

Note that as illustrated in FIGS. 3A and 3B, in the present embodiment, the axial direction of the patient 310 lying supine on the bed 301 is set as the z-axis direction, and the direction from the back surface to the abdomen of the patient 310 is set as the y-axis direction. Furthermore, the direction from the left side to the right side of the patient 310 is set as the x-axis direction.

FIG. 3B is a diagram illustrating the directions of magnetic field lines in a cross-section cut along a line B-B of FIG. 3A, when an alternating magnetic field is generated in the magnetic field generation apparatus 110 in the state illustrated in FIG. 3A. As illustrated in FIG. 3B, the positon where the magnetic field generation apparatus 110 is disposed is adjusted such that the treatment target 311 of the patient 310 is positioned in a normal direction (y-axis direction) with respect to the central portion of the coil 210, so that magnetic field lines (dashed lines in FIG. 3B) can be passed through the treatment target 311 of the patient 310.

Note that the intensity of the alternating magnetic field generated in the magnetic field generation apparatus 110 and applied to the treatment target is, for example, 10 [mT] or more, and preferably 40 [mT] or more.

<Hardware Configuration of Control Unit—First Embodiment>

Figure 4:
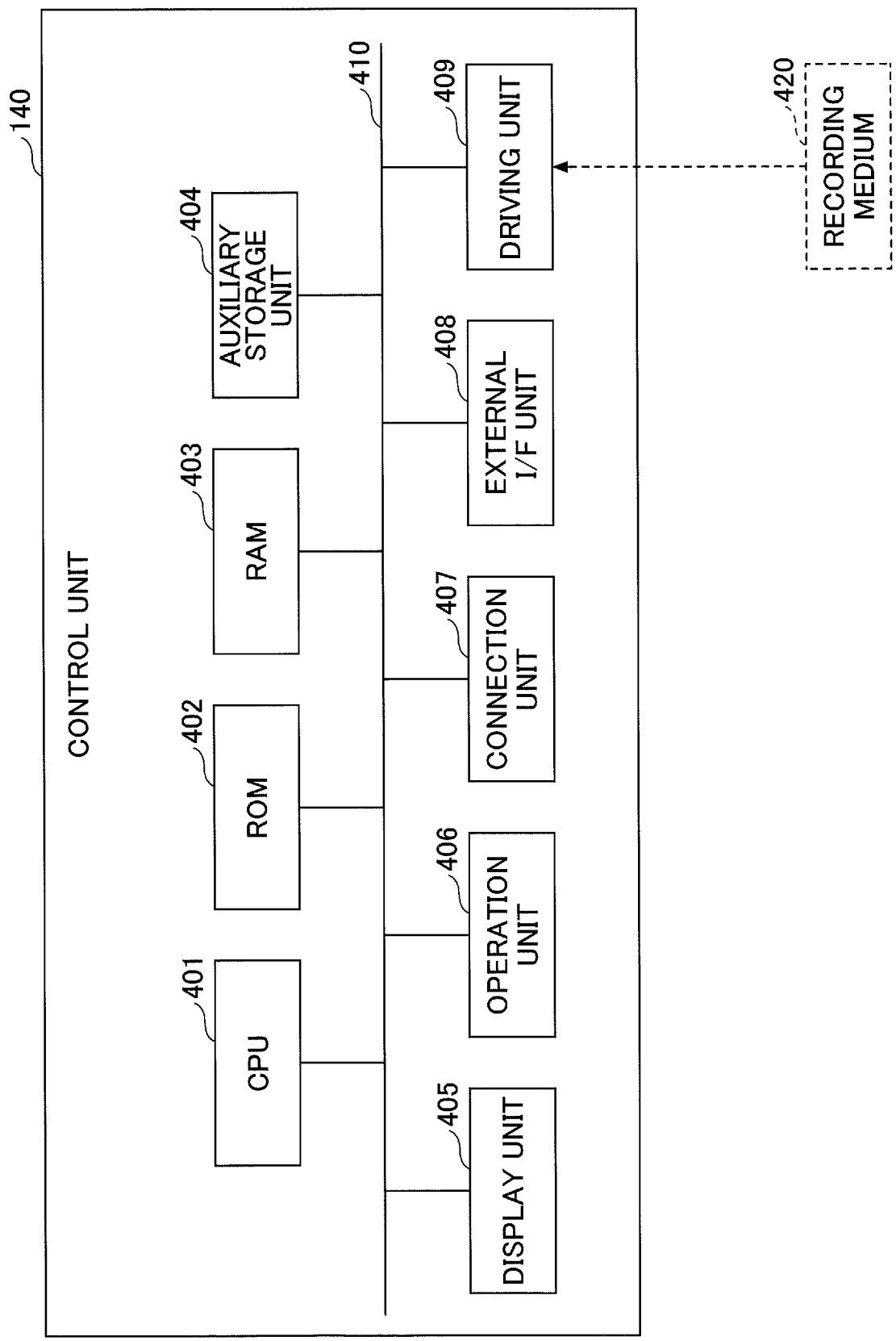
FIG. 4 is a diagram illustrating an example of a hardware configuration of a control unit of a power supply apparatus according to the first embodiment of the present invention.

Next, the hardware configuration of the control unit 140 of the power supply apparatus 120 will be described. FIG. 4 is a diagram illustrating an example of a hardware configuration of the control unit 140 of the power supply apparatus 120.

As illustrated in FIG. 4, the control unit 140 includes a Central Processing Unit (CPU) 401, a Read-Only Memory (ROM) 402, and a Random Access Memory (RAM) 403. The CPU 401, the ROM 402, and the RAM 403 form a so-called computer.

The control unit 140 includes an auxiliary storage unit 404, a display unit 405, an operation unit 406, a connection unit 407, an external interface (I/F) unit 408, and a driving unit 409. The respective hardware elements of the control unit 140 are interconnected via a bus 410.

The CPU 401 is an arithmetic device that executes various programs (e.g., a waveform generation program, etc.) installed in the auxiliary storage unit 404.

The ROM 402 is a non-volatile memory. The ROM 402 functions as a main storage device for storing various programs, data, etc., necessary for the CPU 401 to execute various programs installed in the auxiliary storage unit 404. Specifically, the ROM 402 functions as a main storage device for storing boot programs such as a Basic Input/Output System (BIOS) and an Extensible Firmware Interface (EFI).

RAM 403 is a volatile memory such as a Dynamic Random Access Memory (DRAM) and a Static Random Access Memory (SRAM). The RAM 403 functions as a main storage device for providing a working area that is expanded when various programs installed in the auxiliary storage unit 404 are executed by the CPU 401.

The auxiliary storage unit 404 is an auxiliary storage device for storing various programs and information used when various programs are executed. For example, the waveform information storage unit 160 is implemented in the auxiliary storage unit 404.

The display unit 405 is a display device for displaying a screen, etc., provided by the waveform generating unit 150. The operation unit 406 is an input device used for inputting various instructions to the control unit 140. The connection unit 407 is a connection device for connecting the power supply unit 130 to the control unit 140.

The external I/F unit 408 is a connection device for connecting to any external device. Note that some of the hardware elements of the control unit 140 (for example, any one of the auxiliary storage unit 404, the display unit 405, the operation unit 406, and the driving unit 409, etc.) may be connected via the external I/F unit 408, instead of being included in the control unit 140.

The driving unit 409 is a device for setting a recording medium 420. The recording medium 420 includes a medium that optically, electrically, or magnetically records information, such as a Compact Disk Read-Only Memory (CD-ROM), a flexible disk, an optical magnetic disk, or the like. The recording medium 420 may also include a semiconductor memory or the like that electrically records information, such as a ROM, flash memory, or the like.

Various programs installed in the auxiliary storage unit 404 are installed, for example, by setting the distributed recording medium 420 in the driving unit 409 and reading out various programs recorded in the recording medium 420 by the driving unit 409. Alternatively, various programs installed in the auxiliary storage unit 404 may be installed by being downloaded from a network.

<Example of Waveform Information—First Embodiment>

Next, the waveform information stored in the waveform information storage unit 160 will be described. FIG. 5 is a diagram illustrating an example of waveform information. As illustrated in FIG. 5, waveform information 500 includes "waveform type", "frequency spectrum", and "waveform data" as items of information.

In "waveform type", information indicating the waveform type (in the example illustrated in FIG. 5, the waveform type is simply represented by a Roman number) is stored. Here, the waveform type includes a frequency (waveform) that is effective in inhibiting the growth of a certain type of cancer cells. Accordingly, in "waveform type", for example, the frequency per se may be stored, instead of storing a Roman numeral, as information indicating the waveform type. Alternatively, information indicating the type of cancer for which cancer cells are to be inhibited from growing, may be stored.

In "frequency spectrum", the frequency spectrum of the waveform data stored in the corresponding "waveform data", is stored. According to the waveform information 500, the frequency of waveform data 501 of "waveform type"="I" is "f1", and the frequency of waveform data 502 of "waveform type"="II" is "f2". Furthermore, according to the waveform information 500, the frequency of waveform data 503 of "waveform type"="III" is "f3". In "waveform data", the pieces of waveform data 501, 502, and 503, etc., of the respective frequencies are stored.

Note that frequencies that are effective in inhibiting the growth of certain types of cancer cells include, for example, the following frequencies.

Glioblastoma: 227 [kHz]
Malignant melanoma: 196 [kHz]
Tongue cancer: 196 [kHz]
Breast cancer: 280 [kHz]

Accordingly, as the frequencies f1, f2, and f3 in the waveform information 500, for example, the frequencies described above are assigned.

Note that even with respect the same type of cancer, the cancer cells have various properties. Therefore, in order to inhibit the growth of cancer cells, it is desirable to have different modes of magnetic field application, e.g., as described below, even for the same type of cancer.

Glioblastoma mode 1: 196 [kHz]
Glioblastoma mode 2: 227 [kHz]
Glioblastoma mode 3: 280 [kHz]

<Functional Configuration of Waveform Generating Unit Implemented in Control Unit—First Embodiment>

Figure 6:
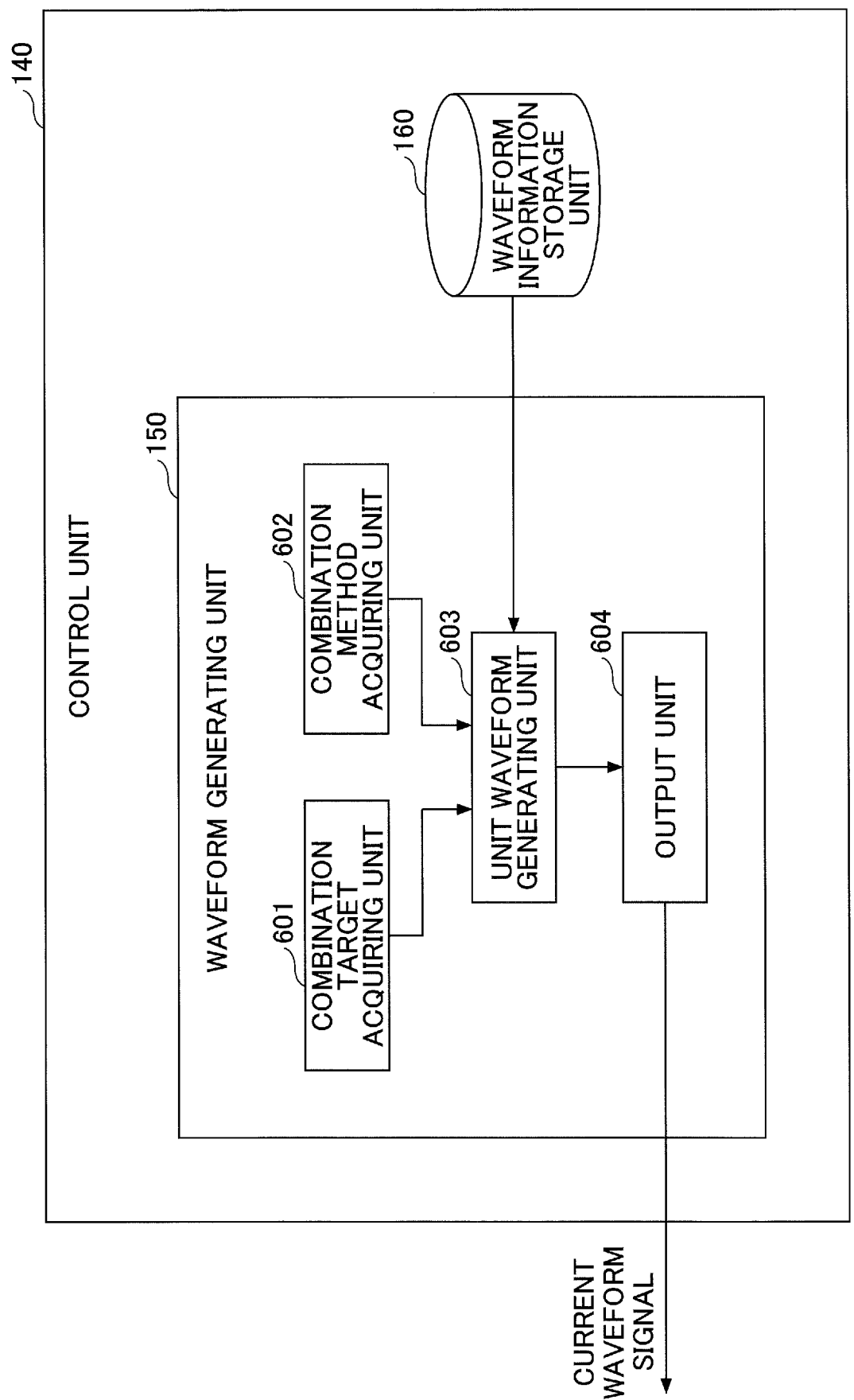
FIG. 6 is a diagram illustrating an example of the functional configuration of a waveform generating unit implemented in the control unit according to the first embodiment of the present invention.

Next, the functional configuration of the waveform generating unit 150 implemented in the control unit 140 will be described. FIG. 6 is a diagram illustrating an example of a functional configuration of the waveform generating unit implemented in the control unit. As illustrated in FIG. 6, the waveform generating unit 150 includes a combination target acquiring unit 601, a combination method acquiring unit 602, a unit waveform generating unit 603, and an output unit 604.

When the combination target acquiring unit 601 combines a plurality of pieces of waveform data to generate a unit waveform pattern, the combination target acquiring unit 601 acquires information identifying the pieces of waveform data to be combined (combination targets). The combination target acquiring unit 601 reports the acquired information to the unit waveform generating unit 603.

The combination target acquiring unit 601 acquires information identifying the waveform data to be combined (combination targets) based on, for example, an instruction from a medical professional such as a physician operating the magnetic field generation system 100.

Note that as information identifying the waveform data to be combined (combination targets), a medical professional, for example, specifies information indicating the waveform type stored in "waveform type" of the waveform information 500. Alternatively, the medical professional may directly specify the frequency or the frequency range of the waveform data to be combined (combination targets). Alternatively, the medical professional may specify the type of cancer for which the growth of cancer cells is desired to be inhibited.

The combination method acquiring unit 602 acquires information specifying a method of combining waveform data to generate a unit waveform pattern by combining a plurality of pieces of waveform data, and reports the acquired information to the unit waveform generating unit 603.

The information specifying the combination method acquired by the combination method acquiring unit 602, includes information specifying either one of the following methods:
a method of combining waveform data to be combined (combination targets) by connecting the waveform data along a time axis; and
a method of combining waveform data to be combined (combination targets) in a superimposed manner in the same time period.

Furthermore, the information specifying the combination method acquired by the combination method acquiring unit 602 includes information specifying either one of the following methods and the magnitude of intensity:
a method of combining waveform data to be combined (combination targets) having different intensities; and
a method of combining waveform data to be combined (combination targets) having the same intensity.

Furthermore, the information specifying the combination method acquired by the combination method acquiring unit 602 includes information specifying either one of the following methods and the ratio of the time length, when the waveform data to be combined (combination targets) is combined by connecting the waveform data along a time axis:
a method of combining the waveform data such that the respective pieces of waveform data have different time lengths; and
a method of combining the waveform data such that the respective pieces of waveform data have the same time length.

Furthermore, information specifying the combination method acquired by the combination method acquiring unit 602 includes information indicating the time from the start of the output to the end of the output of the current waveform signals (application time).

The unit waveform generating unit 603 generates a "unit waveform pattern" having a predetermined time length that is obtained by combining the waveform data to be combined (combination targets).

Specifically, the unit waveform generating unit 603 reads the waveform data from the waveform information storage unit 160 based on the information identifying the waveform data to be combined (combination targets) acquired by the combination target acquiring unit 601.

Furthermore, the unit waveform generating unit 603 generates a unit waveform pattern by combining the waveform data that has been read, based on the information specifying the combination method acquired by the combination method acquiring unit 602. Furthermore, the unit waveform generating unit 603 reports the generated unit waveform pattern to the output unit 604.

The output unit 604 generates and outputs current waveform signals corresponding to the application time, by connecting the unit waveform patterns generated by the unit waveform generating unit 603, along a time axis. Accordingly, the power supply unit 130 can repeatedly apply an alternating current having a unit waveform pattern to the magnetic field generation apparatus 110 during the application time.

<Description of Unit Waveform Pattern—First Embodiment>

Next, specific examples of unit waveform patterns generated by the unit waveform generating unit 603 (here, four specific examples) will be described.

(1) Unit Waveform Pattern 1

Figure 7:
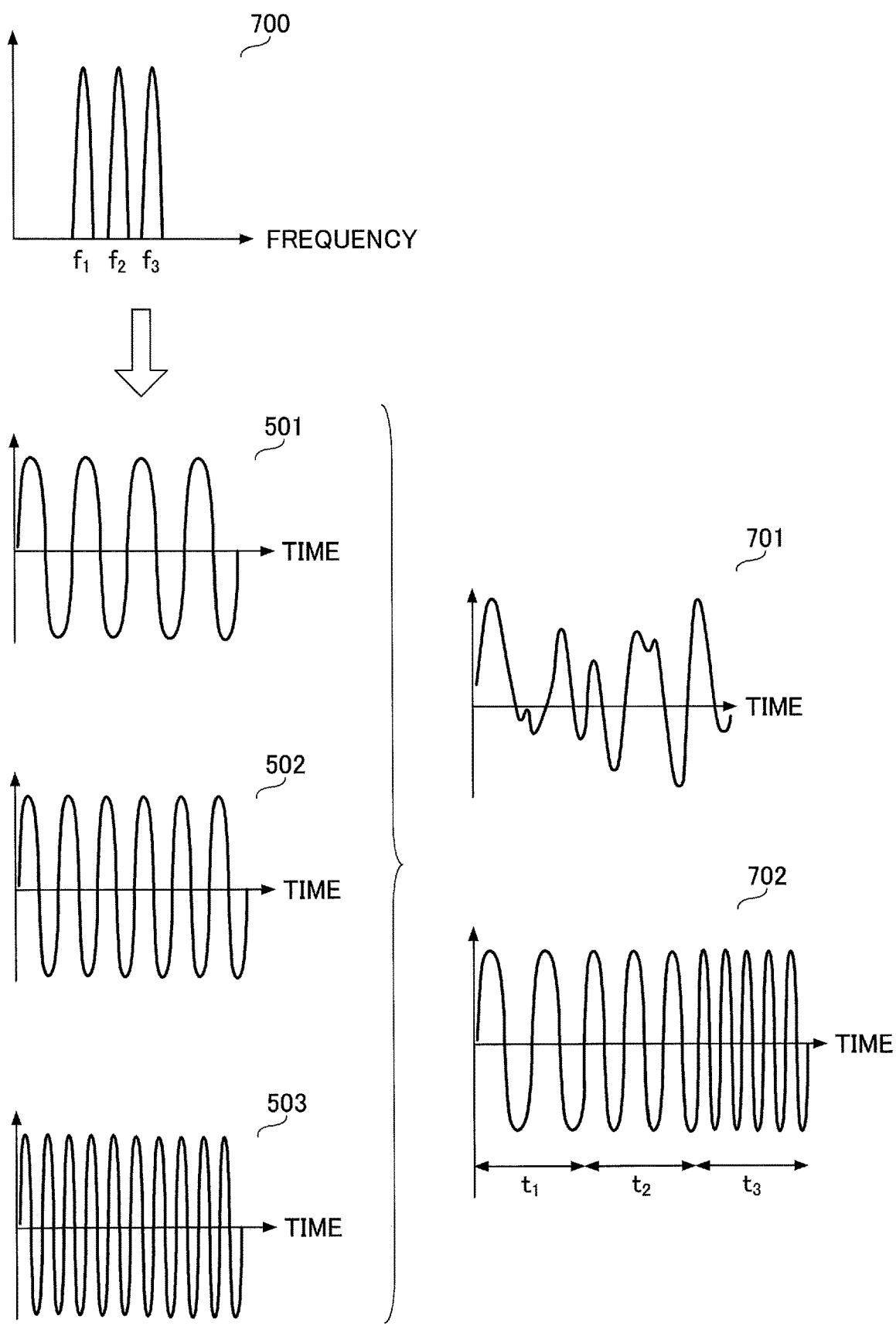
FIG. 7 is a first diagram illustrating an example of a unit waveform pattern according to the first embodiment of the present invention.

FIG. 7 is a first diagram illustrating an example of a unit waveform pattern. The example of FIG. 7 illustrates a case in which the waveform data of the frequency="f1", the waveform data of the frequency="f2", and the waveform data of the frequency="f3" are identified as the waveform data to be combined (combination targets) (see graph 700).

The example of FIG. 7 also illustrates a case in which a method of combining pieces of waveform data to be combined (combination targets) having the same intensity, is specified (see graph 700).

The unit waveform generating unit 603 reads the waveform data 501, 502, and 503 from the waveform information storage unit 160. The unit waveform generating unit 603 also generates a unit waveform pattern 701 or a unit waveform pattern 702 of a predetermined time length based on the read waveform data 501, 502, and 503.

Here, the unit waveform pattern 701 is a unit waveform pattern that is formed when a method of superimposing and combining the waveform data 501, 502, and 503 to be combined (combination targets) in the same time period, is specified.

On the other hand, the unit waveform pattern 702 is a unit waveform pattern that is formed when a method of combining the waveform data 501, 502, and 503 to be combined (combination targets) by connecting the waveform data along a time axis, is specified. Note that, according to the example of FIG. 7, in the case of the unit waveform pattern 702, a method of combining the waveform data 501, 502, and 503 such that the pieces of waveform data have the same time length ($t1=t2=t3$), is further specified.

Note that in the case of the method of superimposing and combining the waveform data as in the case of the unit waveform pattern 701, magnetic fields of the respective frequency components are constantly applied. Thus, it is possible to reduce the time taken to obtain the same effects, as compared to the method of combining the waveform data by connecting the waveform data along a time axis as in the case of the unit waveform pattern 702.

(2) Unit Waveform Pattern 2

Figure 8:
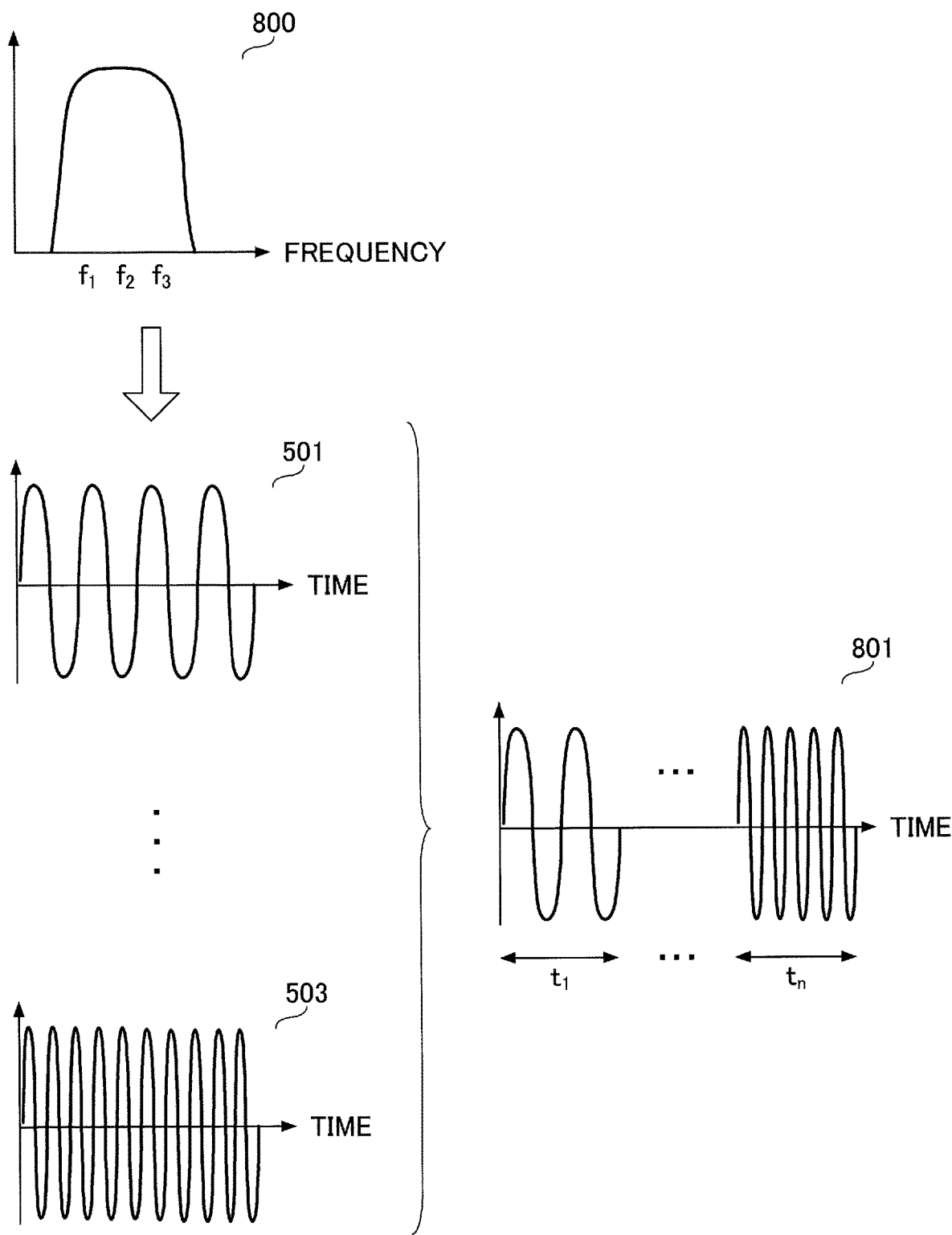
FIG. 8 is a second diagram illustrating an example of a unit waveform pattern according to the first embodiment of the present invention.

FIG. 8 is a second diagram illustrating an example of a unit waveform pattern. The example of FIG. 8 illustrates a case in which the waveform data included in a frequency range from frequency="f1" to frequency="f3" is identified as the waveform data to be combined (combination targets) (see graph 800).

The example of FIG. 8 also illustrates the case in which a method for combining pieces of waveform data to be combined (combination targets) having the same intensity, is specified (see graph 800).

The unit waveform generating unit 603 reads the waveform data of each frequency from the waveform data 501 to the waveform data 503, from the waveform information storage unit 160. Furthermore, the unit waveform generating unit 603 generates a unit waveform pattern 801 having a predetermined time length based on the read waveform data of each frequency.

The unit waveform pattern 801 is a unit waveform pattern that is formed when a method of combining the waveform data of the respective frequencies from the waveform data 501 to the waveform data 503 to be combined (combination targets) by connecting the waveform data along a time axis, is specified. Note that, according to the example of FIG. 8, in the case of the unit waveform pattern 801, a method of combining the waveform data such that the pieces of waveform data have the same time length (t1= . . . =tn), is further specified.

(3) Unit Waveform Pattern 3

Figure 9:
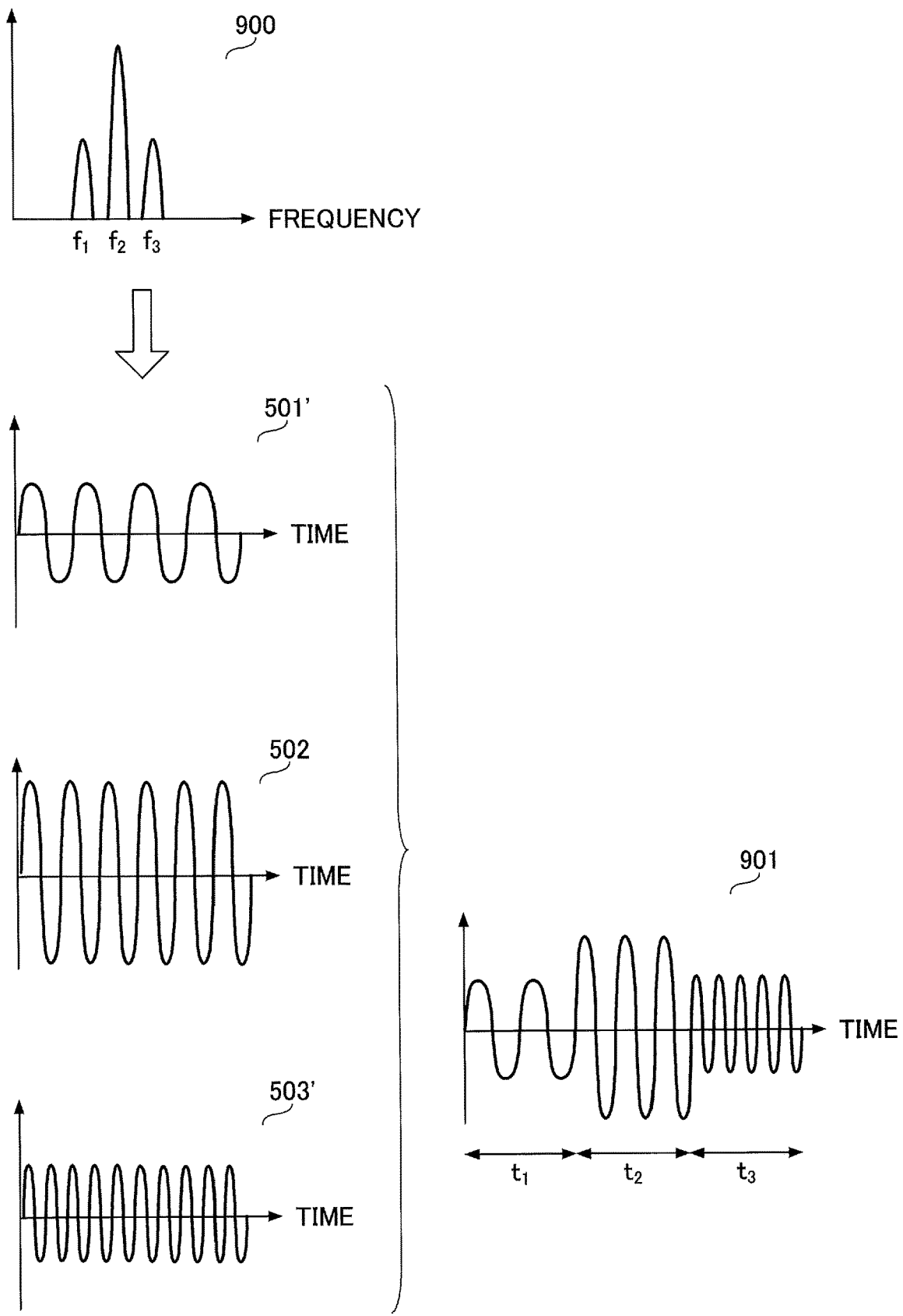
FIG. 9 is a third diagram illustrating an example of a unit waveform pattern according to the first embodiment of the present invention.

FIG. 9 is a third diagram illustrating an example of a unit waveform pattern. The example of FIG. 9 illustrates a case in which the waveform data of frequency="f1", the waveform data of frequency="f2", and the waveform data of frequency="f3" are identified as the waveform data to be combined (combination targets) (see graph 900).

The example of FIG. 9 also illustrates a case in which a method of combining pieces of waveform data to be combined (combination targets) having different intensities, is specified (see graph 900).

The unit waveform generating unit 603 acquires waveform data 501', 502, and 503' from the waveform information storage unit 160. Note that the waveform data 501' is waveform data acquired by correcting the waveform data 501 read from the waveform information storage unit 160, according to a specified intensity. Similarly, the waveform data 503' is waveform data acquired by correcting the waveform data 503 read from the waveform information storage unit 160, according to a specified intensity.

As illustrated in FIG. 9, the unit waveform generating unit 603 generates a unit waveform pattern 901 of a predetermined time length based on the acquired waveform data 501', 502, and 503'.

The unit waveform pattern 901 is a unit waveform pattern formed when a method of combining waveform data 501', 502, and 503' to be combined (combination targets) by connecting the waveform data along a time axis, is specified. Note that, according to the example of FIG. 9, in the case of the unit waveform pattern 901, a method of combining the waveform data such that the pieces of waveform data have the same time length (t1=t2=t3), is further specified.

(4) Unit Waveform Pattern 4

Figure 10:
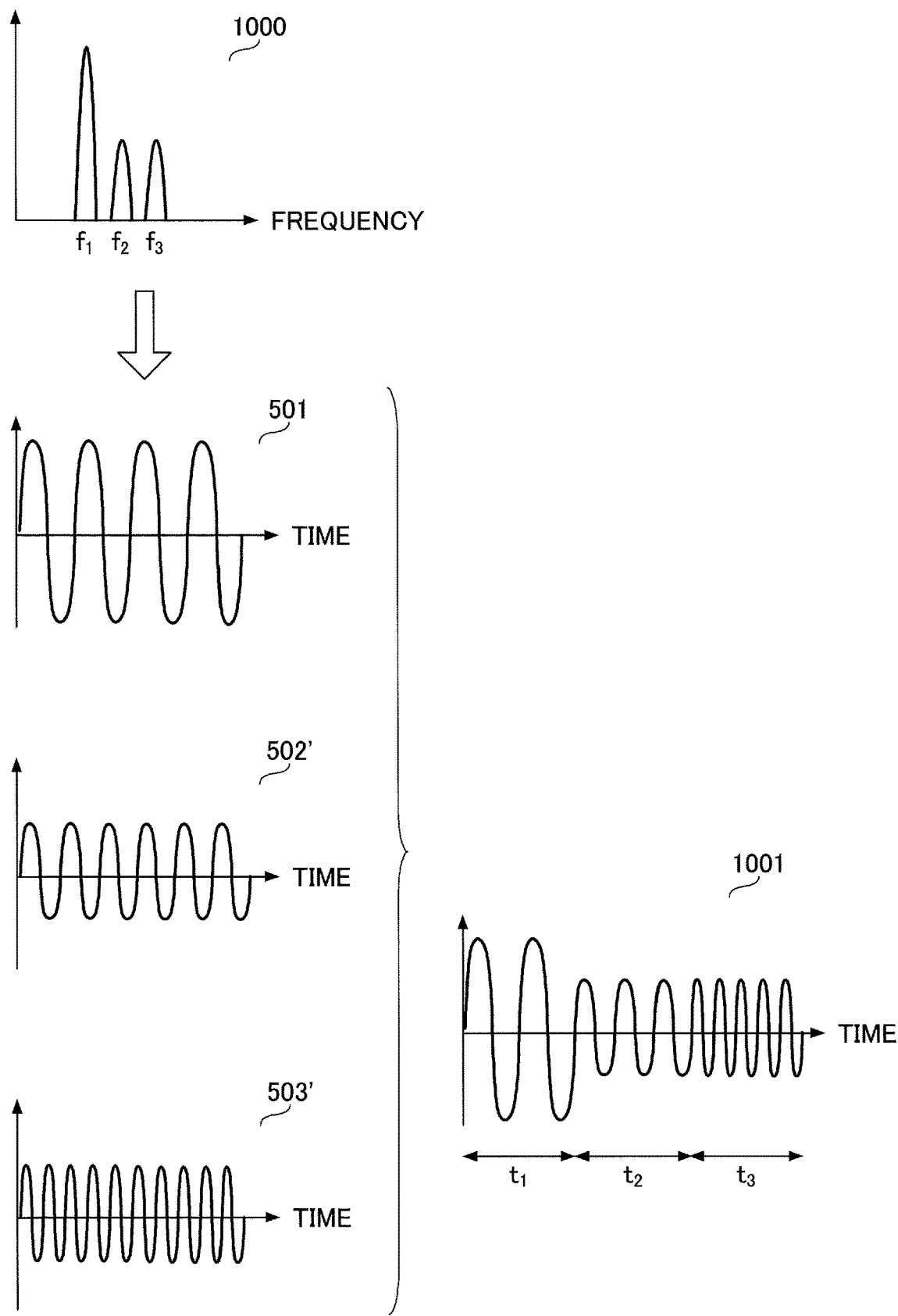
FIG. 10 is a fourth diagram illustrating an example of a unit waveform pattern according to the first embodiment of the present invention.

FIG. 10 is a fourth diagram illustrating an example of a unit waveform pattern. The example of FIG. 10 illustrates the case in which the waveform data of the frequency="f1", the waveform data of the frequency="f2", and the waveform data of the frequency="f3" are identified as the waveform data to be combined (combination targets) (see graph 1000).

The example of FIG. 10 also illustrates a case in which a method of combining pieces of waveform data to be combined (combination targets) having different intensities, is specified (see graph 900).

The unit waveform generating unit 603 acquires the waveform data 501, 502', and 503' from the waveform information storing unit 160. The waveform data 502' is waveform data acquired by correcting the waveform data 502 read from the waveform information storage unit 160, according to a specified intensity. Similarly, the waveform data 503' is waveform data acquired by correcting the waveform data 503 read from the waveform information storage unit 160, according to a specified intensity.

As illustrated in FIG. 10, the unit waveform generating unit 603 generates a unit waveform pattern 1001 of a predetermined time length, based on the acquired waveform data 501, 502', and 503'.

The unit waveform pattern 1001 is a unit waveform pattern that is formed when a method of combining the waveform data 501, 502', and 503' to be combined (combination targets) by connecting the waveform data along a time axis, is specified. Note that, according to the example of FIG. 10, in the case of the unit waveform pattern 1001, a method of combining the waveform data such that the pieces of waveform data have the same time length (t1=t2=t3), is further specified.

<Specific Examples of Current Waveforms Signals—First Embodiment>

Figure 11:
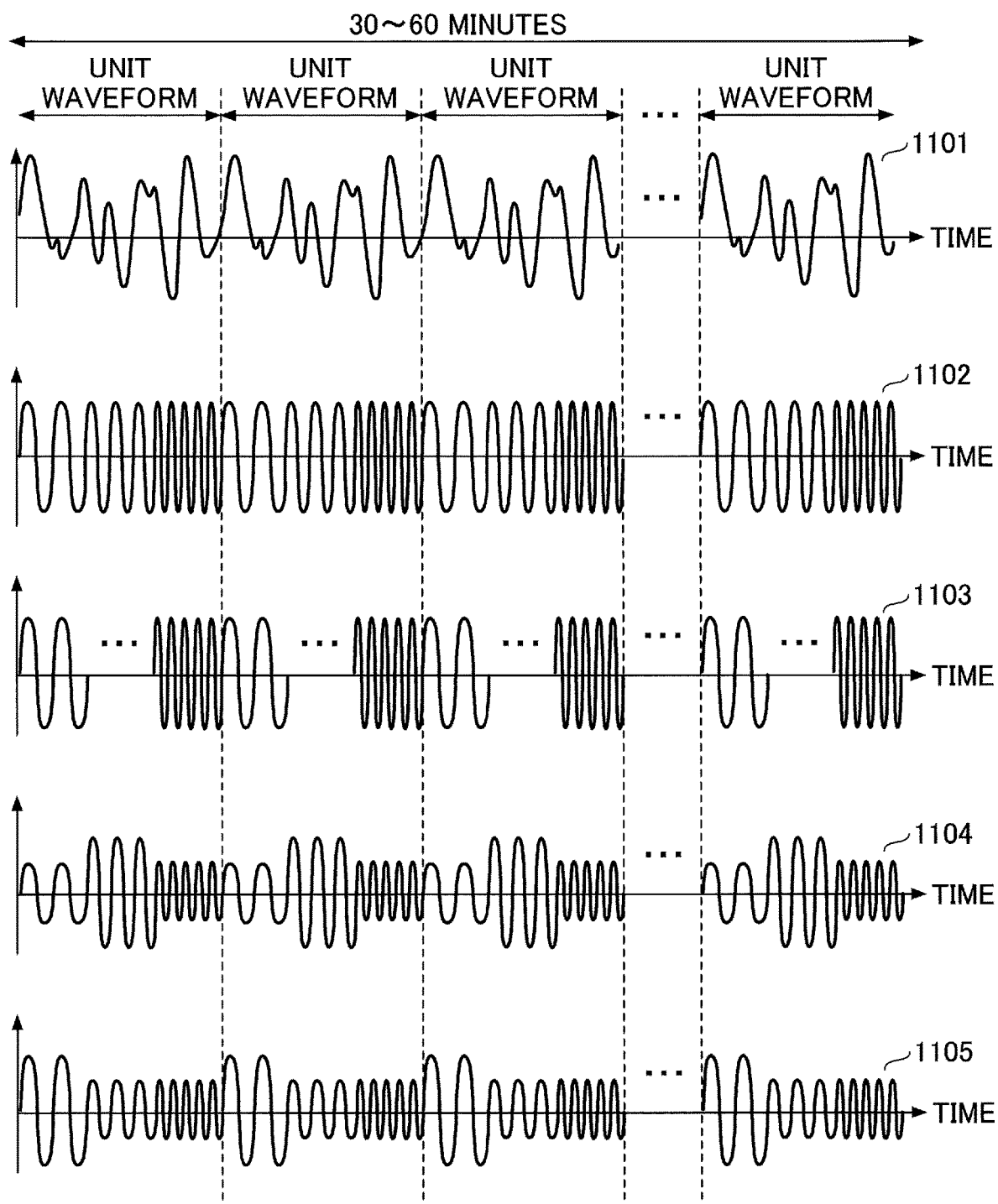
FIG. 11 is a diagram illustrating a specific example of current waveform signals according to the first embodiment of the present invention.

Next, specific examples of current waveform signals generated by the output unit 604 will be described. FIG. 11 is a diagram illustrating specific examples of current waveform signals. As illustrated in FIG. 11, when a unit waveform pattern is acquired from the unit waveform generating unit 603, the output unit 604 connects the acquired unit waveform patterns during the application time (e.g., 30 minutes to 60 minutes), thereby generating current waveform signals.

In FIG. 11, current waveform signals 1101 are current waveform signals generated by connecting the unit waveform patterns 701. Furthermore, current waveform signals 1102 are current waveform signals generated by connecting the unit waveform patterns 702. Hereinafter, similarly, current waveform signals 1103 to 1105 are current waveform signals generated by connecting the unit waveform patterns 801 to 1001, respectively.

As described above, the control unit 140 controls the alternating current applied by the power supply unit 130 by transmitting, to the power supply unit 130, current waveform signals obtained by connecting the unit waveform patterns including a plurality of pieces of waveform data having different frequency spectrums from each other.

<User Interface of Control Unit—First Embodiment>

Figure 12:
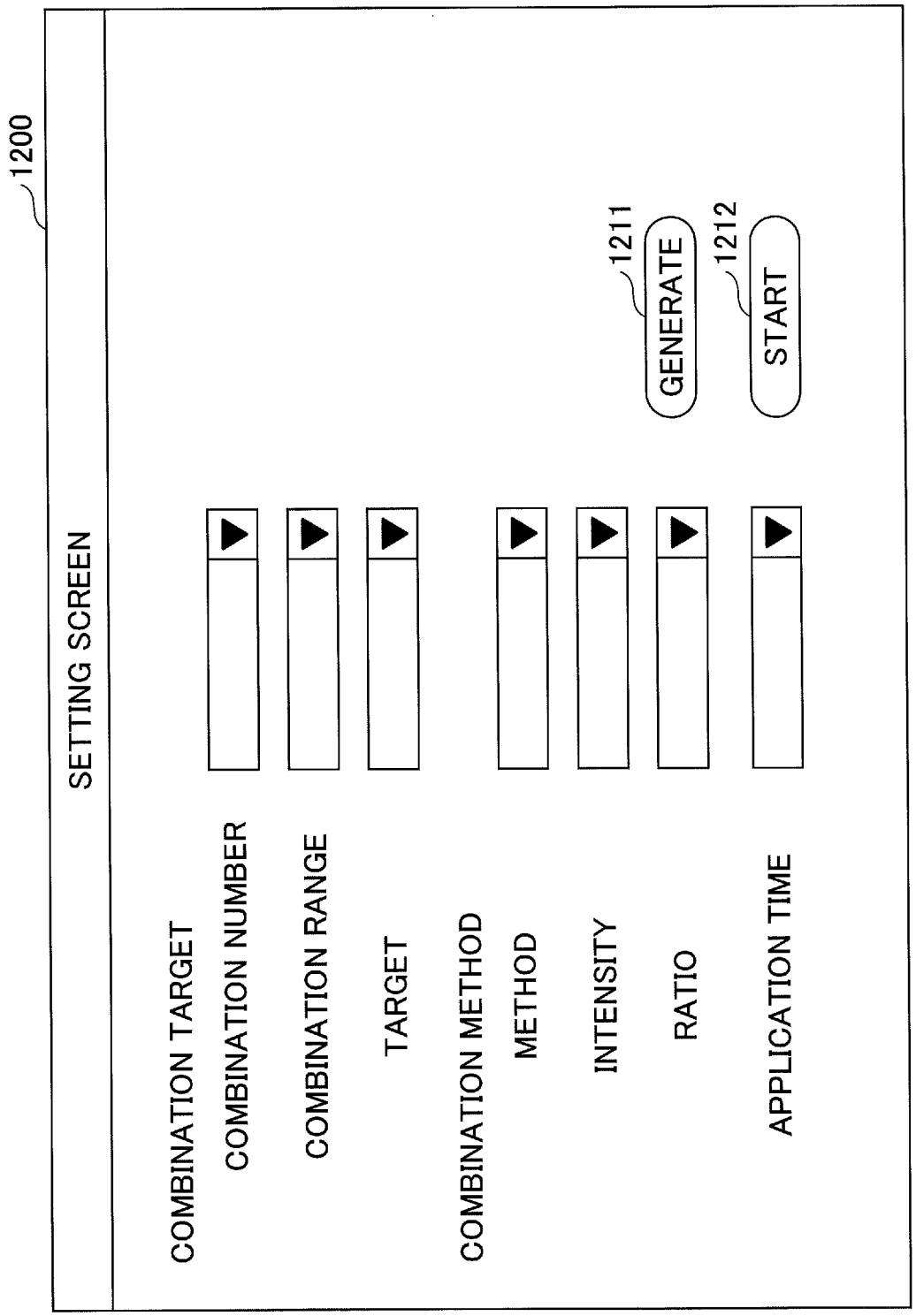
FIG. 12 is a diagram illustrating an example of a user interface provided by the control unit according to the first embodiment of the present invention.

Next, a user interface provided by the waveform generating unit 150 of the control unit 140 will be described. FIG. 12 is a diagram illustrating an example of a user interface provided by the control unit. When the waveform generating unit 150 is activated in the control unit 140, the display unit 405 displays a setting screen 1200.

As illustrated in FIG. 12, the setting screen 1200 includes an area for inputting information identifying combination targets, an area for inputting information specifying a combination method, and an area for setting the application time.

The area for inputting information identifying combination targets includes "combination number", "combination range", and "target" as input items.

In the "combination number", the number of pieces of waveform data when combining a plurality of pieces of waveform data to generate a unit waveform pattern, is input. In the "combination range", information about whether the pieces of waveform data to be combined (combination targets) are to be individually identified or to be identified as a frequency range, is input. In the "target", information identifying the waveform data to be combined, is input. As described above, in "target", information indicating the waveform type stored in the "waveform type" of the waveform information 500, or a frequency or a frequency range of the waveform data to be combined, may be input. Alternatively, the type of cancer cells to be inhibited from growing, may be input.

The area for inputting information specifying the combination method includes "method", "intensity", and "ratio" as input items.

As the "method", information specifying either one of the following methods may be input:
a method combining waveform data to be combined (combination targets) by connecting the waveform data along a time axis; and
a method of combining waveform data to be combined (combination targets) in a superimposed manner in the same time period.

As "intensity", information specifying either one of the following methods and the magnitude of the intensity may be input:
a method of combining waveform data to be combined (combination targets) having different intensities; and
a method of combining waveform data to be combined (combination targets) having the same intensity.

As "ratio", information specifying either one of the following methods and the ratio of the time length, when the waveform data to be combined (combination targets) is combined by connecting the waveform data along a time axis, may be input:
a method of combining the waveform data such that the respective pieces of waveform data have different time lengths; and
a method of combining the waveform data such that the respective pieces of waveform data have the same time length.

The area for setting the application time includes "application time" as an input item. As the "application time", an application time (e.g., in the range of 30 minutes to 60 minutes) is input.

The setting screen 1200 further includes a generate button 1211 and a start button 1212. Upon completion of inputting each input item included in the area for inputting information identifying the combination targets and each input item included in the area for inputting information specifying the combination method, the generate button 1211 turns into a state of being able to be pressed (or clicked, etc.). In this state, when the generate button 1211 is pressed, the unit waveform generating unit 603 generates a unit waveform pattern.

Furthermore, when the start button 1212 is pressed in a state where the unit waveform pattern is generated, the output unit 604 generates current waveform signals based on the generated unit waveform pattern and transmits the current waveform signals to the power supply unit 130.

<Flow of Magnetic Field Application Process—First Embodiment>

Figure 13:
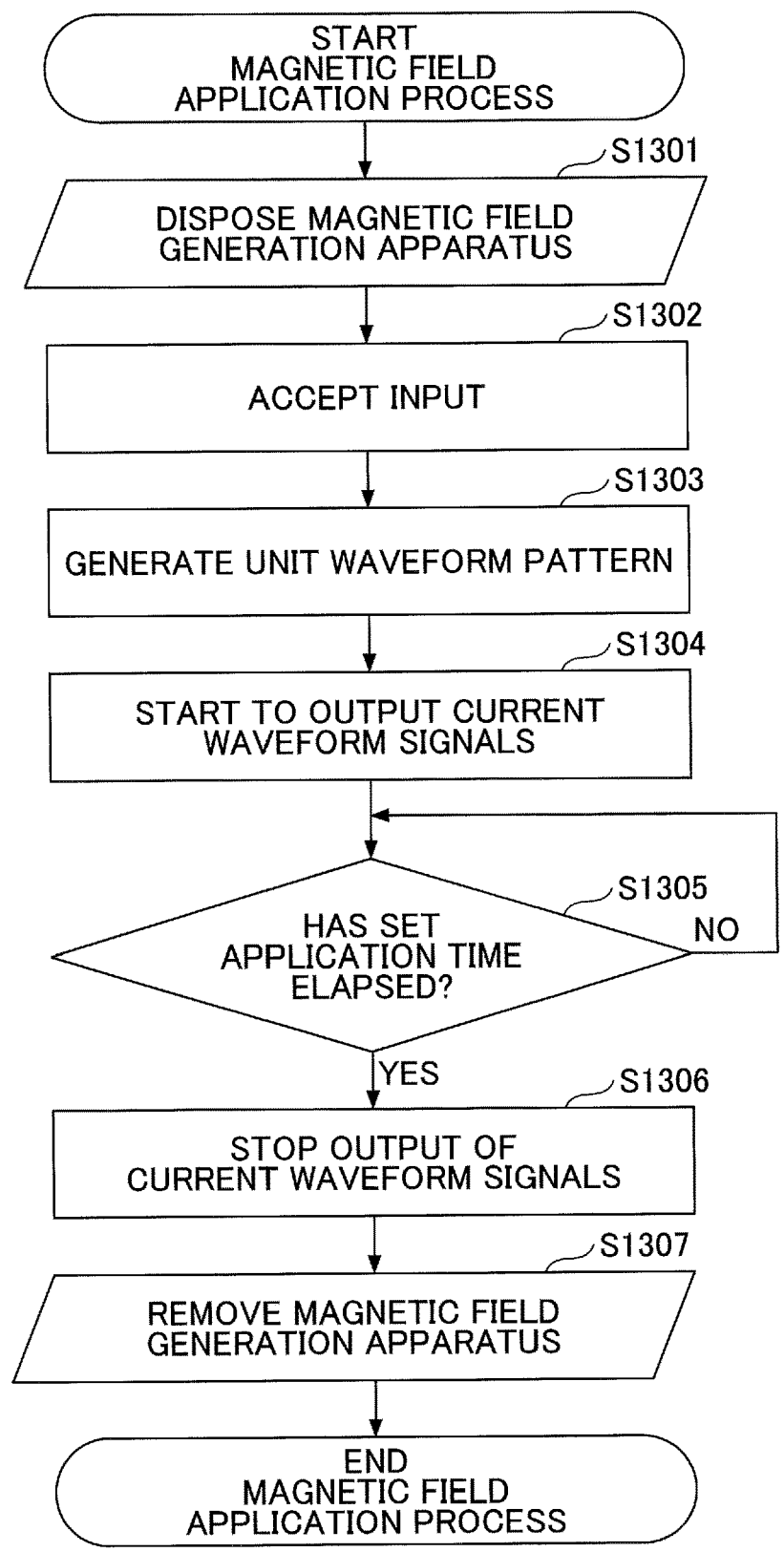
FIG. 13 is a flowchart illustrating a flow of a magnetic field application process by the magnetic field generation system according to the first embodiment of the present invention.

Next, the flow of the entire magnetic field application process by the magnetic field generation system 100 will be described. FIG. 13 is a flow chart illustrating the flow of a magnetic field application process by the magnetic field generation system. As illustrated in FIG. 13, in step S1301, the medical professional disposes the magnetic field generation apparatus 110 at a position corresponding to the position of the treatment target 311 of the patient 310.

In step S1302, the control unit 140 accepts input of each input item from the medical professional via the setting screen 1200. In step S1303, the control unit 140 generates a unit waveform pattern.

In step S1304, the control unit 140 starts to output current waveform signals, and the power supply unit 130 applies an alternating current corresponding to the current waveform signals, to the magnetic field generation apparatus 110. Thus, an alternating magnetic field is generated in the magnetic field generation apparatus 110 and an alternating magnetic field is applied to the treatment target 311 of the patient 310.

In step S1305, the control unit 140 determines whether the set application time has elapsed. When the control unit 140 determines, in step S1305, that the set application time has not elapsed (NO in step S1305), the control unit 140 waits until the set application time elapses.

In contrast, when the control unit 140 determines in step S1305 that the set application time has elapsed (YES in step S1305), the process proceeds to step S1306. In step S1306, the control unit 140 stops the output of the current waveform signals.

In step S1307, the medical professional removes the magnetic field generation apparatus 110 disposed at the position corresponding to the position of the treatment target 311 of the patient 310 and ends the magnetic field application process.

<Overview—First Embodiment>

As is apparent from the above description, the magnetic field generation system 100 according to the first embodiment has the following features.

A power supply unit that applies an alternating current to a magnetic field generation apparatus, is included.

A control unit that transmits current waveform signals to control the alternating current applied by the power supply, is included.

Furthermore, in the magnetic field generation system 100 according to the first embodiment, the control unit generates a unit waveform pattern including a plurality of current waveforms having different frequency spectrums from each other, and generates current waveform signals by connecting the generated unit waveform patterns.

Thus, the magnetic field generation system 100 according to the first embodiment generates a unit waveform pattern having a wide range of frequencies by combining different frequencies, with respect to a particular frequency that is effective in inhibiting the growth of cancer cells. Furthermore, an alternating current having the generated unit waveform patterns is repeatedly applied to the magnetic field generation apparatus.

This improves the effect of inhibiting the growth of cancer cells, even when the cancer cells have various properties. That is, the magnetic field generation system 100 according to the first embodiment can provide a power supply apparatus and a magnetic field generation system capable of applying an alternating magnetic field of an appropriate frequency.

Second Embodiment

In the first embodiment described above, different frequencies are combined in order to improve the effectiveness of inhibiting the growth of cancer cells. On the other hand, in a second embodiment, the intensity of an alternating magnetic field applied to the cancer cells is increased, in order to improve the effectiveness of inhibiting the growth of cancer cells.

Note that in order to increase the intensity of the alternating magnetic field applied to cancer cells, it is effective to reduce the distance between the magnetic field generation apparatus and the treatment target. The intensity of the alternating magnetic field depends on the distance from the magnetic field generation apparatus, and by bringing the magnetic field generation apparatus closer to the treatment target, the intensity of the alternating magnetic field applied to the cancer cells can be increased, even if the alternating current applied to the magnetic field generation apparatus is the same.

Thus, in the second embodiment, the magnetic field generation apparatus is configured to be placed near the treatment target of the patient. Hereinafter, the second embodiment will be described by mainly focusing on the difference from the first embodiment described above.

<System Configuration of Magnetic Field Generation System—Second Embodiment>

Figure 14:
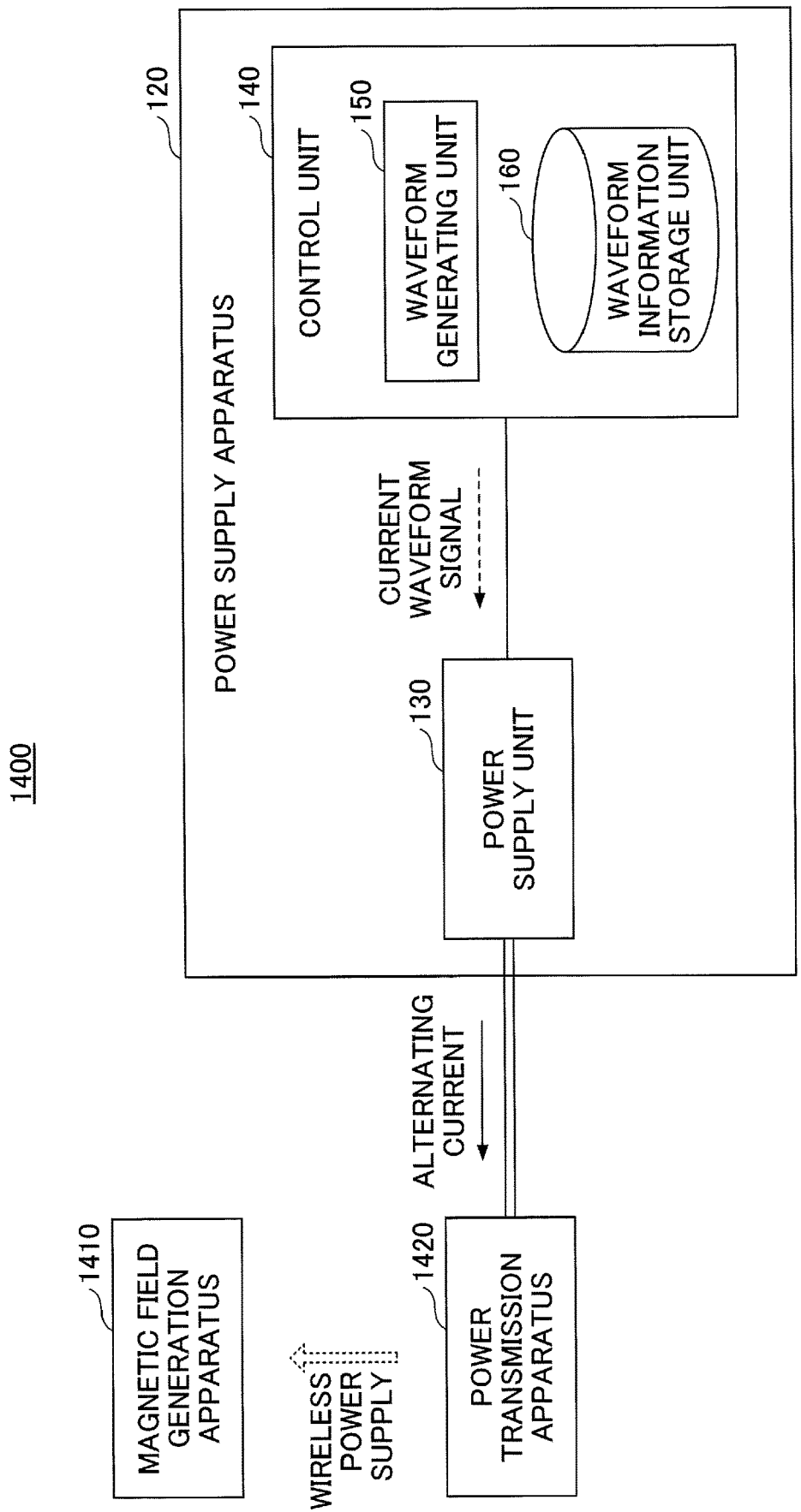
FIG. 14 is a diagram illustrating an example of a system configuration of a magnetic field generation system according to a second embodiment of the present invention.

First, the system configuration of the magnetic field generation system according to the second embodiment will be described. FIG. 14 is a diagram illustrating an example of the system configuration of a magnetic field generation system 1400 according to the second embodiment. The difference from the magnetic field generation system 100 described in the first embodiment above with reference to FIG. 1, is that the magnetic field generation system 1400 includes a magnetic field generation apparatus 1410 and a power transmission apparatus 1420.

The magnetic field generation apparatus 1410 is placed near the treatment target 311 within the body of the patient 310 by surgery or the like. The magnetic field generation apparatus 1410 includes a power receiving coil of a magnetic field resonance type, in addition to a coil formed in a swirl-like shape. In the magnetic field generation apparatus 1410, the power receiving coil receives an alternating current that is wirelessly supplied from the power transmission apparatus 1420, so that the alternating current flows to the coil formed in a swirl-like shape, thereby generating an alternating magnetic field.

The power transmission apparatus 1420 is disposed outside the body of the patient 310 and near the magnetic field generation apparatus 1410. The power transmission apparatus 1420 includes a power transmission coil and a core and wirelessly supplies power to the magnetic field generation apparatus 1410 by a magnetic field resonance method.

<Positional Relationship between Direction of Magnetic Field Line and Treatment Target—Second Embodiment>

Figure 15A:
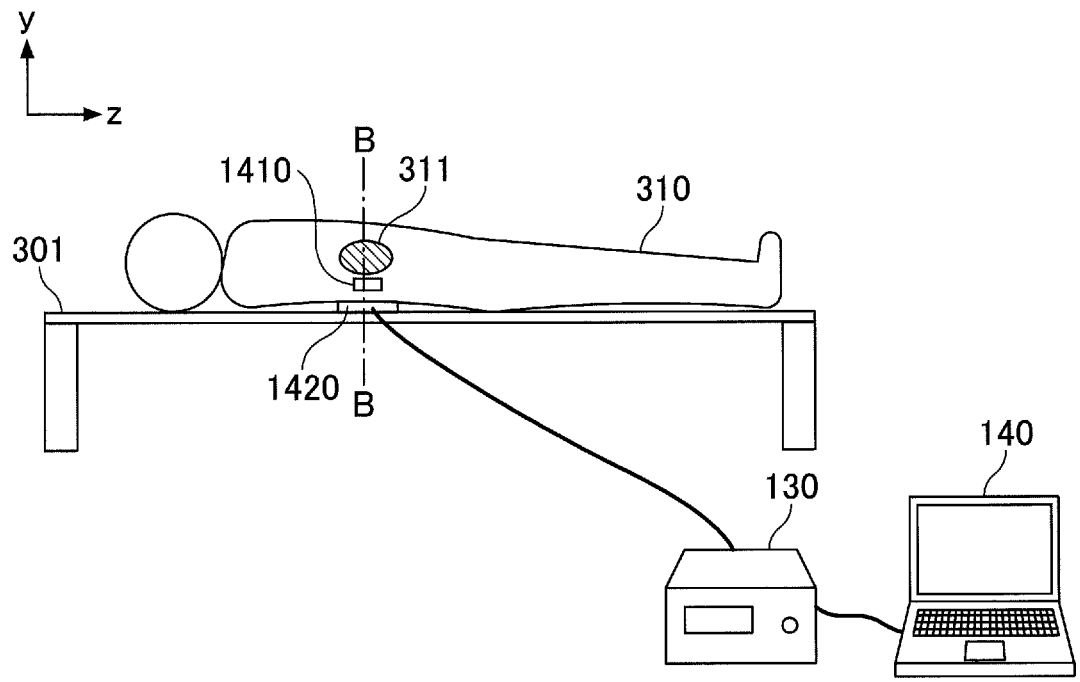
FIGS. 15A and 15B are diagrams illustrating a positional relationship between directions of magnetic field lines of the magnetic field generation apparatus and a diseased portion (treatment target) according to the second embodiment of the present invention.
Figure 15B:
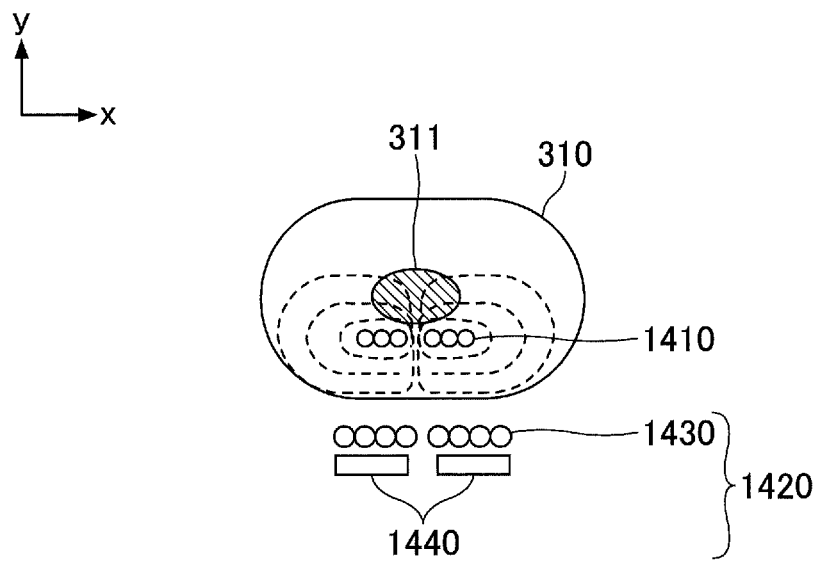

Next, a description is given of the positional relationship between the directions of magnetic field lines and the treatment target, when an alternating magnetic field is generated in the magnetic field generation apparatus 1410, will be described. FIGS. 15A and 15B are diagrams illustrating a positional relationship between directions of magnetic field lines of the magnetic field generation apparatus and the treatment target.

As illustrated in FIG. 15A, the magnetic field generation apparatus 1410 is placed near the treatment target 311 of the patient 310. The power transmission apparatus 1420 is disposed near the magnetic field generation apparatus 1410.

FIG. 15B illustrates a B-B cross-section of FIG. 15A. In the state illustrated in FIG. 15A, by applying an alternating current to a power transmission coil 1430, the magnetic field generation apparatus 1410 receives power by a power receiving coil (not illustrated). This causes an alternating current to flow to the magnetic field generation apparatus 1410 so that an alternating magnetic field is generated.

As illustrated in FIG. 15B, the magnetic field generation apparatus 1410 placed inside the body of the patient 310 generates an alternating magnetic field, thereby allowing multiple magnetic field lines (dashed lines in FIG. 15B) to pass through the treatment target 311 of the patient 310. That is, the intensity of the alternating magnetic field applied to the treatment target 311 of the patient 310 can be increased. As a result, it is possible to improve the effect of inhibiting the growth of cancer cells.

<Overview—Second Embodiment>

As is apparent from the above description, the magnetic field generation system 1400 according to the second embodiment includes the magnetic field generation apparatus that generates an alternating magnetic field upon receiving power that is wirelessly supplied, and a power transmission apparatus that wirelessly supplies power to the magnetic field generation apparatus, and the magnetic field generation apparatus is placed near the treatment target of the patient.

This allows alternating magnetic field to be generated near the treatment target of the patient, and the intensity of the alternating magnetic field applied to the cancer cells is increased. That is, the magnetic field generation system 100 according to the second embodiment can provide a power supply apparatus and a magnetic field generation system capable of applying an alternating magnetic field of an appropriate intensity.

Third Embodiment

In the second embodiment described above, the magnetic field generation apparatus is placed near the treatment target in order to reduce the distance between the magnetic field generation apparatus and the treatment target and increase the intensity of the alternating magnetic field applied to the cancer cells. On the other hand, in a third embodiment, the magnetic field generation apparatus is configured to be inserted into the patient's body. Hereinafter, the third embodiment will be described by mainly focusing on the difference from the first embodiment described above.

Figure 16:
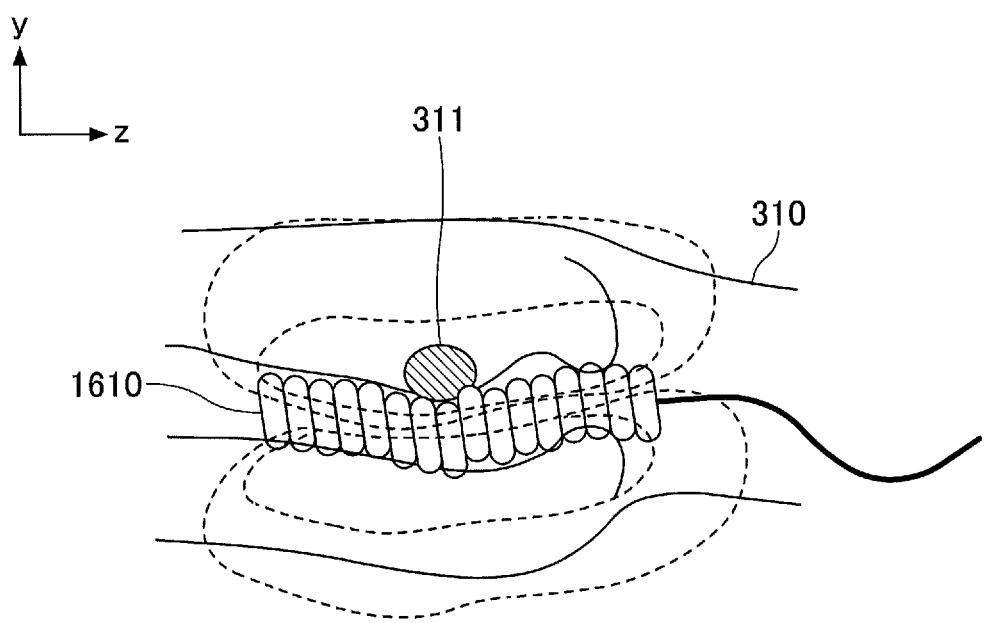
FIG. 16 is a first diagram illustrating another configuration example of the magnetic field generation apparatus according to a third embodiment of the present invention.

FIG. 16 is a first diagram illustrating another configuration example of a magnetic field generation apparatus. As illustrated in FIG. 16, in the third embodiment, the coil configuring the magnetic field generation apparatus is formed in a helical shape and is wound around a flexible rod-like member so as to be deformable, such that when inserted into the body of the patient 310, the central axis of the helical shape follows the curve of a body cavity.

Accordingly, an alternating magnetic field having a higher intensity can be applied to the treatment target 311, as compared to applying an alternating magnetic field to the treatment target 311 from outside the body of the patient 310. The example of FIG. 16 illustrates a case that in order to increase the intensity of the alternating magnetic field applied to cancer cells of the rectal cancer, a medical professional has inserted a magnetic field generation apparatus 1610 into the anus of the patient 310 and has moved the magnetic field generation apparatus 1610 to a position near the cancer cells of the rectal cancer.

Note that the mode of inserting the magnetic field generation apparatus 1610 into the body of the patient 310 is not limited to the above; for example, in order to increase the intensity of the alternating magnetic field applied to the cancer cells of an esophageal cancer, a medical professional may insert the magnetic field generation apparatus into the mouth of the patient 310 and move the magnetic field generation apparatus to a position near the cancer cells of the esophageal cancer.

Furthermore, the shape of the coil forming the magnetic field generation apparatus is not limited to a helical shape. For example, a plurality of coils formed in a swirl-like shape may be disposed on the same plane, and the coils may be connected with at least a flexible member so as to be deformable, such that when the coils are inserted into the body of the patient 310, the connecting axis connecting the respective connection points of the coils follows the curve of a body cavity.

As described above, the coil forming the magnetic field generation apparatus is configured to be deformable so that the coil can be inserted into the body of the patient 310 and can be moved in the body cavity to a position near cancer cells of any type of cancer.

Fourth Embodiment

In the second and third embodiments described above, a configuration in which the distance between the magnetic field generation apparatus and the treatment target is reduced, in order to increase the intensity of the alternating magnetic field applied to the cancer cells, is described. On the other hand, a fourth embodiment describes a configuration in which a magnetic flux density is increased in order to increase the intensity of the alternating magnetic field applied to the cancer cells.

Figure 17A:
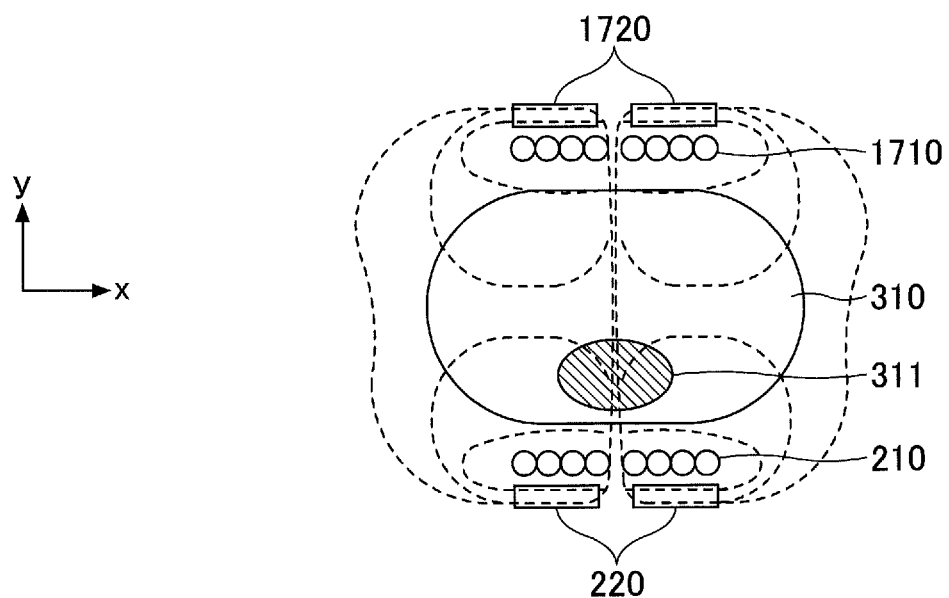
FIGS. 17A and 17B are second diagrams illustrating another configuration example of the magnetic field generation apparatus according to a fourth embodiment of the present invention.
Figure 17B:
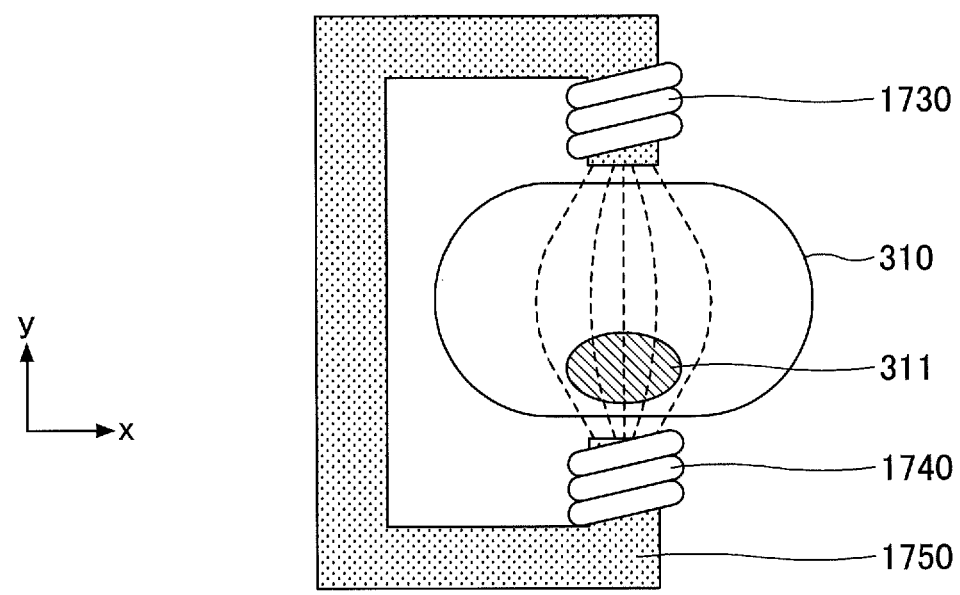

FIGS. 17A and 17B are second diagrams illustrating another configuration example of a magnetic field generation apparatus. Among these figures, FIG. 17A illustrates a configuration in which two magnetic field generation apparatuses (coils 210 and 1710, cores 220 and 1720) are disposed on the back side and the ventral side of the treatment target 311 of the patient 310, to increase the intensity of the alternating magnetic field applied to the treatment target 311. As described above, by increasing the number of magnetic field generation apparatuses, the intensity of the alternating magnetic field applied to the treatment target 311 can be increased.

Note that in the example illustrated in FIG. 17A, two magnetic field generation apparatuses are disposed in the y-axis direction with the treatment target 311 sandwiched therebetween. However, two magnetic field generation apparatuses may be disposed in the x-axis direction with the treatment target 311 sandwiched therebetween. Furthermore, in the example illustrated in FIG. 17A, a case of disposing two magnetic field generation apparatuses is described; however, three or more magnetic field generation apparatuses may be disposed.

FIG. 17B illustrates a configuration in which two magnetic field generation apparatuses are disposed on the back side and the ventral side of the treatment target 311 of the patient 310 to increase the intensity of the alternating magnetic field applied to the treatment target 311. The difference from FIG. 17A is that coils 1730 and 1740 included in the magnetic field generation apparatuses are formed in a helical shape rather than a swirl-like shape. Furthermore, a second difference from FIG. 17A is that a core 1750 shaped as a C-arm is inserted into the central portion of each of the helically formed coils.

In the configuration illustrated in FIG. 17B, the alternating magnetic field generated by one coil 1730 is directed to the other coil 1740, thereby reducing the leakage magnetic field and increasing the intensity of the alternating magnetic field applied to the treatment target 311.

Thus, by changing the number of pieces, the shape, the arrangement, etc., of the magnetic field generation apparatus, the intensity of the alternating magnetic field applied to the cancer cells can be increased. That is, according to the magnetic field generation system of the fourth embodiment, it is possible to provide a power supply apparatus and a magnetic field generation system capable of applying an alternating magnetic field of an appropriate intensity.

Fifth Embodiment

In the first to fourth embodiments described above, a case in which a magnetic field generation apparatus is configured to apply an alternating magnetic field to a treatment target of a patient positioned in a normal direction with respect to a central portion of a coil of the magnetic field generation apparatus, has been described. On the other hand, in a fifth embodiment, a case in which the magnetic field generation apparatus is configured to apply an alternating magnetic field to the treatment target of the patient positioned at the central portion of the coil of the magnetic field generation apparatus, will be described.

Figure 18A:
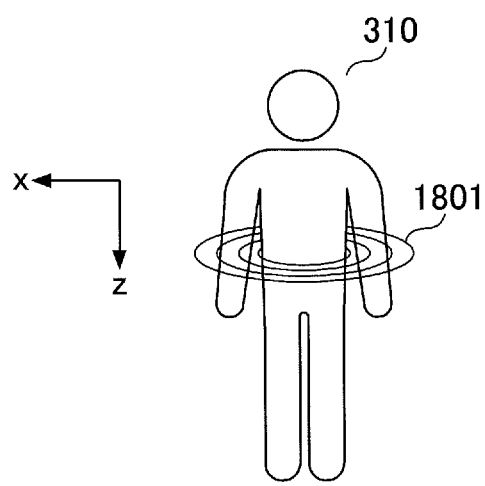
FIGS. 18A to 18D are third diagrams illustrating another configuration example of the magnetic field generation apparatus according to a fifth embodiment of the present invention.
Figure 18B:
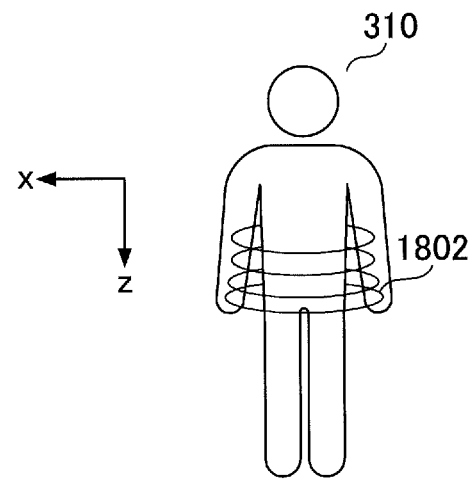

FIGS. 18A to 18D are third diagrams illustrating another configuration example of a magnetic field generation apparatus. Among these diagrams, FIG. 18A illustrates a magnetic field generation apparatus configured such that a torso portion of the patient 310 is disposed at a central portion of a swirl-like coil 1801. FIG. 18B illustrates a magnetic field generation apparatus configured such that the torso portion of the patient 310 is disposed at the central portion of a helical coil 1802. By the configurations as illustrated in FIGS. 18A and 18B, an alternating magnetic field can be applied to the treatment target of the patient located at the central portion of the coil of the magnetic field generation apparatus.

Figure 18C:
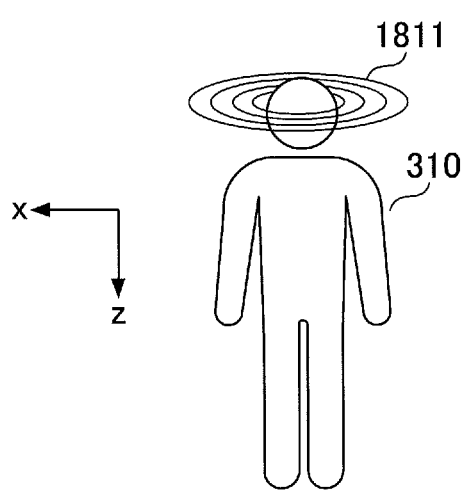
Figure 18D:
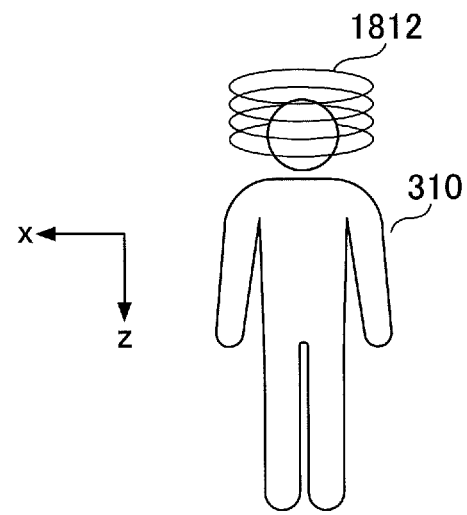

Similarly, FIG. 18C illustrates a magnetic field generation apparatus configured such that the head of the patient 310 is positioned at the central portion of a swirl-like coil 1811. FIG. 18D illustrates a magnetic field generation apparatus configured such that the head of the patient 310 is positioned at the central portion of a helical coil 1812. By the configurations as illustrated in FIGS. 18C and 18D, an alternating magnetic field can be applied to the treatment target of the patient located at the central portion of the coil of the magnetic field generation apparatus.

Other Embodiments

In the first embodiment described above, the combination target, the combination method, the application time and the like are input regardless of the number of pieces, the shape, the arrangement, etc., of the magnetic field generation apparatus. However, the combination target, the combination method, the application time and the like may be input depending on the number of pieces, the shape, the arrangement and the like of the magnetic field generation apparatus.

Furthermore, in the first embodiment described above, in the setting screen 1200, a medical professional inputs each input item of a combination target and a combination method. However, a medical professional may select one of the patterns of combination targets and combination methods that are input in advance, to input the combination target and the combination method.

Furthermore, in the first embodiment described above, the power supply unit 130 and the control unit 140 are described as separate units in the power supply apparatus 120. However, the power supply unit 130 and the control unit 140 may be integrally configured.

According to one embodiment of the present invention, a power supply apparatus and a magnetic field generation system applying an appropriate alternating magnetic field.

The power supply apparatus and the magnetic field generation system are not limited to the specific embodiments described in the detailed description, and variations and modifications may be made without departing from the spirit and scope of the present invention.

What is claimed is:

1. A power supply apparatus comprising:
a power supply configured to apply an alternating current to a magnetic field generation apparatus;
a waveform information storage unit configured to store a plurality of predetermined sets of different waveform types including a plurality of different frequency spectrums and a plurality of different waveform data, and
a controller configured to control the alternating current applied by the power supply, wherein
the controller combines at least two sets of the plurality of different wave data to generate a waveform pattern and controls the power supply to apply the alternating current having the waveform pattern including a plurality of current waveforms having different frequency spectrums from each other.

2. The power supply apparatus according to claim 1, wherein the controller controls the power supply to apply the alternating current having the waveform pattern in which the plurality of current waveforms, which have different frequency spectrums, are connected along a time axis.

3. The power supply apparatus according to claim 2, wherein the controller controls the power supply to apply the alternating current having the waveform pattern in which the plurality of current waveforms, which have different frequency spectrums, are connected along the time axis so as to have different time lengths.

4. The power supply apparatus according to claim 1, wherein the controller controls the power supply to apply the alternating current having the waveform pattern in which the plurality of current waveforms, which have different frequency spectrums, are superimposed.

5. The power supply apparatus according to claim 1, wherein the controller controls the power supply to repeatedly apply the alternating current during a predetermined time length.

6. A magnetic field generation system comprising:
the power supply apparatus according to claim 1; and
the magnetic field generation apparatus.

7. The power supply apparatus according to claim 1, wherein the controller controls a screen provided to the power supply apparatus to display a first area for inputting information identifying the at least two sets of the different waveform types, a second area for inputting information specifying a combination method of the at least two sets of the different waveform types, and a third area for setting the application time of the alternating current having the waveform pattern.

8. A magnetic field generation system comprising:
a magnetic field generation apparatus;
a power supply configured to apply an alternating current to the magnetic field generation apparatus;
a waveform information storage unit configured to store a plurality of predetermined sets of different waveform types including a plurality of different frequency spectrums and a plurality of different waveform data, and
a controller configured to control the alternating current applied by the power supply, combine at least two sets of the plurality of different wave data to generate a waveform pattern and control the power supply to apply the alternating current having the waveform pattern including a plurality of current waveforms having different frequency spectrums from each other, wherein
the magnetic field generation apparatus is formed of a coil having a helical shape, or is formed by connecting a plurality of coils so as to overlap in radial directions of the coils, and a central axis of the helical shape or a connection axis connecting center points of the plurality of coils is deformable so as to conform to a curved shape along a body cavity of a patient.

9. The magnetic field generation system according to claim 8, wherein the controller controls the power supply to apply the alternating current having a waveform pattern including a plurality of current waveforms having different frequency spectrums from each other, wherein the controller controls the power supply to apply the alternating current having the waveform pattern by applying one of the plurality of current waveforms and subsequently applying another one of the plurality of current waveforms so as to connecting the one of the plurality of current waveforms and the another one of the plurality of current waveforms along a time axis.

10. A magnetic field generation system comprising:
a magnetic field generation apparatus that is provided within a human body;
a power transmission apparatus configured to wirelessly supply power to the magnetic field generation apparatus; and
a power supply apparatus including
a power supply configured to apply an alternating current to the power transmission apparatus,
a waveform information storage unit configured to store a plurality of predetermined sets of different waveform types including a plurality of different frequency spectrums and a plurality of different waveform data, and
a controller configured to control the alternating current applied by the power supply, combine at least two sets of the plurality of different wave data to generate a waveform pattern and control the power supply to apply the alternating current having the waveform pattern including a plurality of current waveforms having different frequency spectrums from each other.

11. The magnetic field generation system according to claim 10, wherein the power transmission apparatus wirelessly supplies the power by magnetic field resonance.

\* \* \* \* \*